United States Patent
Beardsley

(10) Patent No.: US 11,504,120 B2
(45) Date of Patent: *Nov. 22, 2022

(54) STAPLE FEEDING AND FORMING APPARATUS

(71) Applicant: Covidien LP, Mansfield, MA (US)

(72) Inventor: John Beardsley, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 99 days.

This patent is subject to a terminal disclaimer.

(21) Appl. No.: 16/890,338

(22) Filed: Jun. 2, 2020

(65) Prior Publication Data

US 2020/0289114 A1    Sep. 17, 2020

Related U.S. Application Data

(63) Continuation of application No. 15/205,087, filed on Aug. 17, 2016, now Pat. No. 10,702,268, which is a
(Continued)

(51) Int. Cl.
*A61B 17/06* (2006.01)
*A61B 17/072* (2006.01)
(Continued)

(52) U.S. Cl.
CPC ........ *A61B 17/072* (2013.01); *A61B 17/0644* (2013.01); *A61B 17/0682* (2013.01);
(Continued)

(58) Field of Classification Search
CPC ................................. B25C 5/16; B25C 5/1637
(Continued)

(56) References Cited

U.S. PATENT DOCUMENTS 2,127,665 A    8/1938    Leslie
3,080,564 A    3/1963    Strekopov et al.
(Continued)

FOREIGN PATENT DOCUMENTS

WO    03094745 A1    11/2003
WO    2009033057 A2    3/2009

OTHER PUBLICATIONS

European Search Report dated Jan. 22, 2013 issued by the European Patent Office in corresponding European Patent Application No. EP12186174.4 (8 pages).
(Continued)

*Primary Examiner* — Thanh K Truong
*Assistant Examiner* — Patrick B Fry
(74) *Attorney, Agent, or Firm* — Carter, Deluca & Farrell LLP

(57) ABSTRACT

Disclosed is a surgical stapling apparatus and method of use that includes a cartridge assembly which is capable of being reloaded during a surgical procedure without being removed from the surgical site. This allows a surgeon to continue a surgical operation without withdrawing or removing the surgical stapler for reloading and thus reduces the length of the surgery while allowing the physician to concentrate solely on the surgical procedure rather than dividing attention between the surgical procedure and reloading of the surgical stapler. The surgical stapling apparatus includes an elongate member having a plurality of fasteners arranged in a plurality of longitudinally extending rows which is longitudinally translatable through the cartridge to position the plurality of fasteners relative to a plurality of retention slots extending through an upper surface of the cartridge.

6 Claims, 20 Drawing Sheets

Related U.S. Application Data continuation of application No. 15/204,502, filed on Jul. 7, 2016, now Pat. No. 10,639,033, which is a continuation of application No. 13/762,511, filed on Feb. 8, 2013, now Pat. No. 9,402,628, which is a continuation of application No. 13/281,888, filed on Oct. 26, 2011, now Pat. No. 8,418,908.

(51) Int. Cl.
*B25C 5/16* (2006.01)
*A61B 17/064* (2006.01)
*A61B 17/068* (2006.01)

(52) U.S. Cl.
CPC .... *A61B 17/0686* (2013.01); *A61B 17/07207* (2013.01); *A61B 2017/07271* (2013.01); *A61B 2017/07278* (2013.01)

(58) Field of Classification Search
USPC ........................................... 227/176.1
See application file for complete search history.

(56) References Cited

U.S. PATENT DOCUMENTS

| | | | | |
|---|---|---|---|---|
| 3,650,453 A | * | 3/1972 | Smith, Jr. | A61B 17/0684 |
| | | | | 227/138 |
| 3,717,294 A | * | 2/1973 | Green | A61B 17/0684 |
| | | | | 227/19 |
| 3,837,555 A | | 9/1974 | Green | |
| 3,899,914 A | | 8/1975 | Akiyama | |
| 4,127,227 A | * | 11/1978 | Green | A61B 17/0684 |
| | | | | 227/19 |
| 4,378,065 A | | 3/1983 | Smirne | |
| 4,475,679 A | | 10/1984 | Fleury, Jr. | |
| 4,762,260 A | | 8/1988 | Richards | |
| 4,951,860 A | | 8/1990 | Peters et al. | |
| 4,969,591 A | * | 11/1990 | Richards | A61B 17/0644 |
| | | | | 227/132 |
| 5,456,400 A | | 10/1995 | Shichman et al. | |
| 5,662,260 A | | 9/1997 | Yoon | |
| 5,865,361 A | | 2/1999 | Milliman et al. | |
| 5,919,198 A | | 7/1999 | Graves, Jr. et al. | |
| 6,817,508 B1 | | 11/2004 | Racenet et al. | |
| 7,588,175 B2 | | 9/2009 | Timm et al. | |
| 7,651,017 B2 | | 1/2010 | Ortiz et al. | |
| 7,810,692 B2 | | 10/2010 | Hall et al. | |
| 7,819,296 B2 | | 10/2010 | Hueil et al. | |
| 7,954,683 B1 | | 6/2011 | Knodel et al. | |
| 7,963,432 B2 | | 6/2011 | Knodel et al. | |
| 8,056,789 B1 | | 11/2011 | White et al. | |
| 8,070,036 B1 | * | 12/2011 | Knodel | A61B 17/07207 |
| | | | | 227/175.1 |
| 8,096,457 B1 | | 1/2012 | Manoux et al. | |
| 8,240,538 B1 | | 8/2012 | Manoux | |
| 8,261,958 B1 | | 9/2012 | Knodel | |
| 8,272,551 B2 | | 9/2012 | Knodel et al. | |
| 8,418,908 B1 | * | 4/2013 | Beardsley | A61B 17/0644 |
| | | | | 227/176.1 |
| 8,636,189 B1 | | 1/2014 | Knodel et al. | |
| 8,763,876 B2 | * | 7/2014 | Kostrzewski | A61B 17/105 |
| | | | | 227/176.1 |
| 8,789,739 B2 | | 7/2014 | Swensgard | |
| 8,931,679 B2 | | 1/2015 | Kostrzewski | |
| 9,402,628 B2 | | 8/2016 | Beardsley | |
| 10,702,268 B2 | | 7/2020 | Beardsley | |
| 2010/0179559 A1 | | 7/2010 | Walker | |
| 2013/0001270 A1 | * | 1/2013 | Kostrzewski | A61B 17/068 |
| | | | | 227/176.1 |

OTHER PUBLICATIONS

European Search Report EP12186174.4-1654 dated May 22, 2015.

* cited by examiner

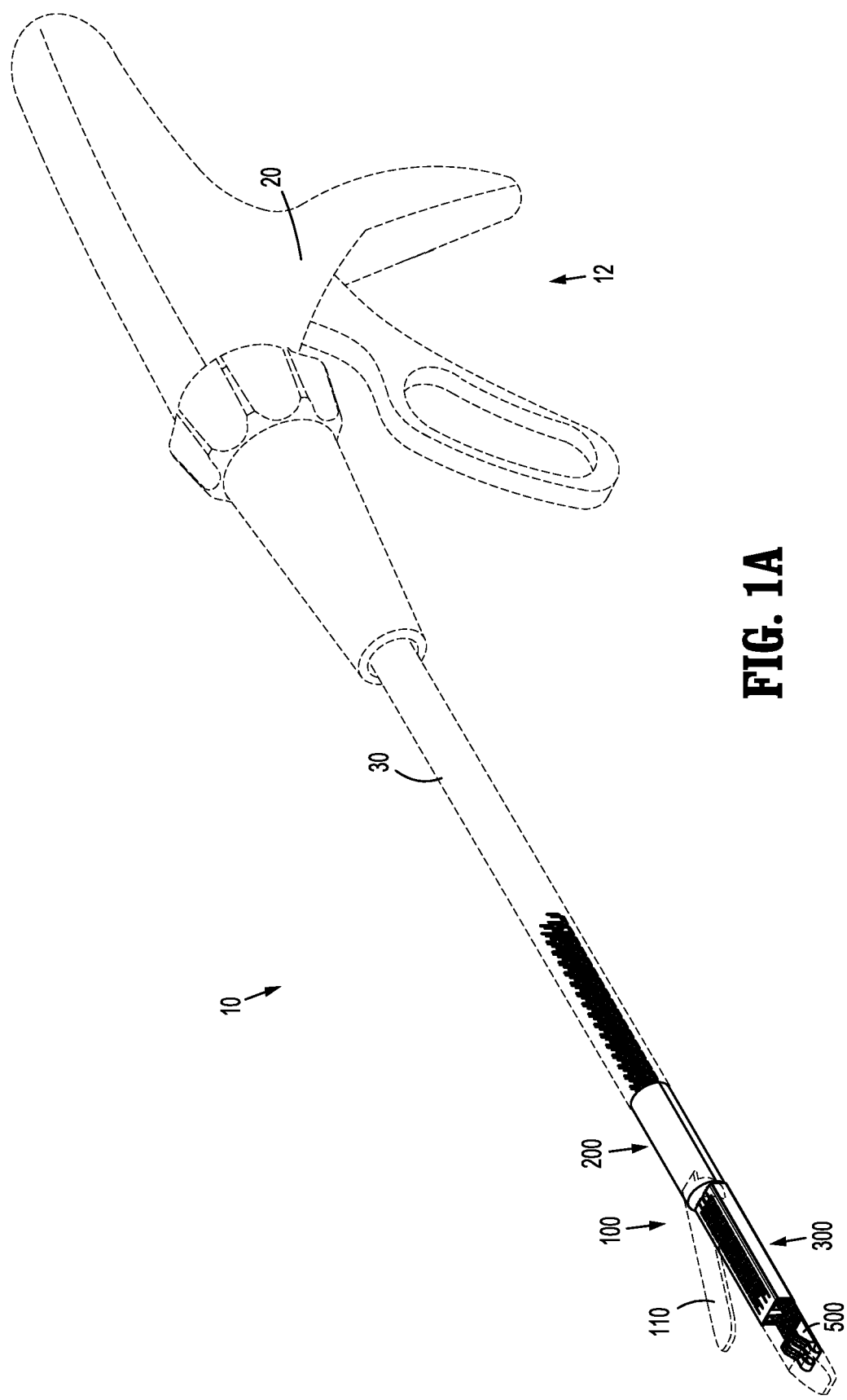

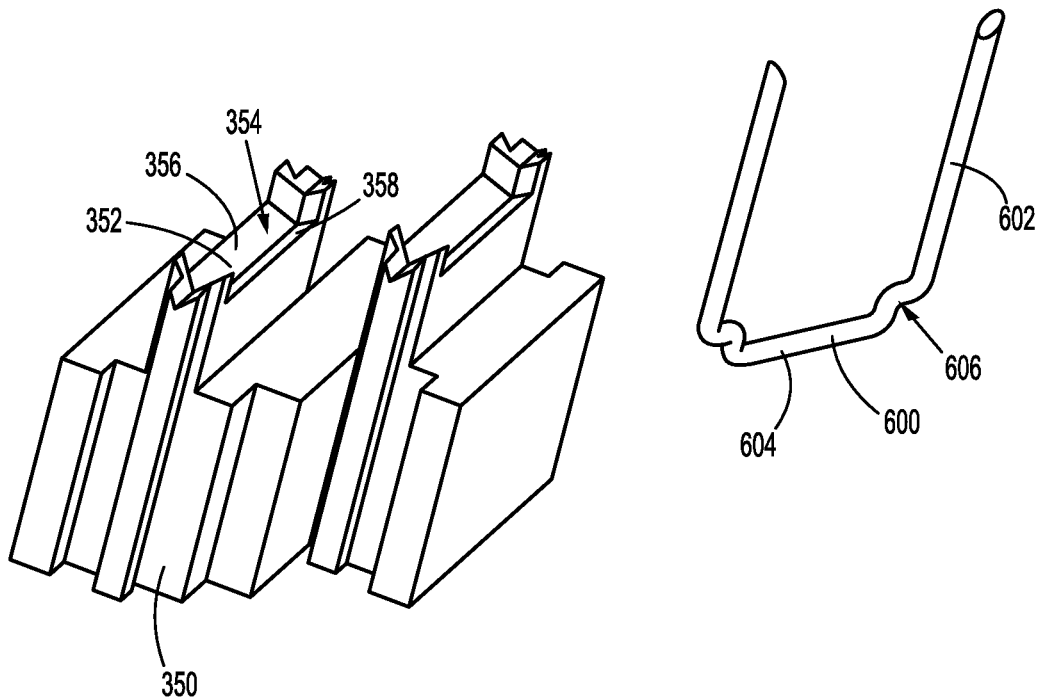
FIG. 6A
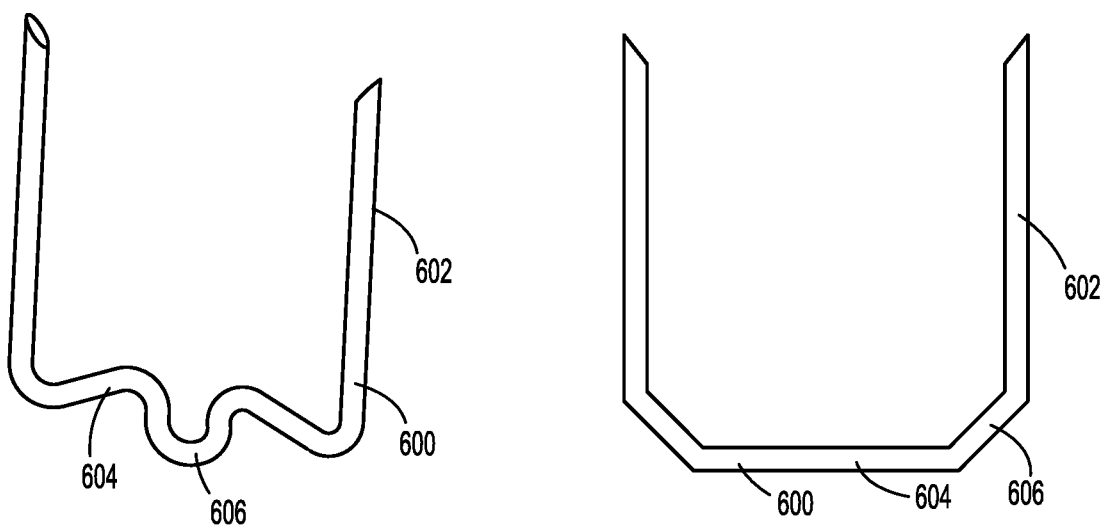
FIG. 6B
FIG. 6C

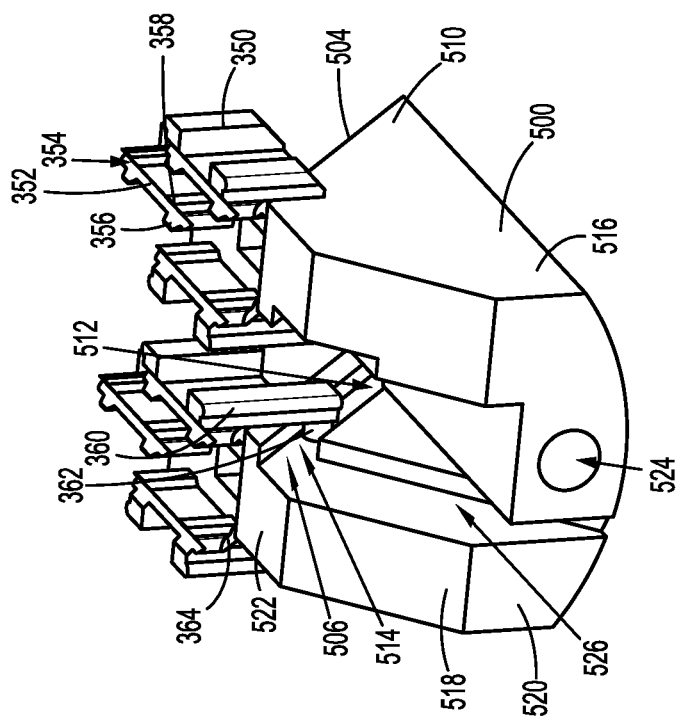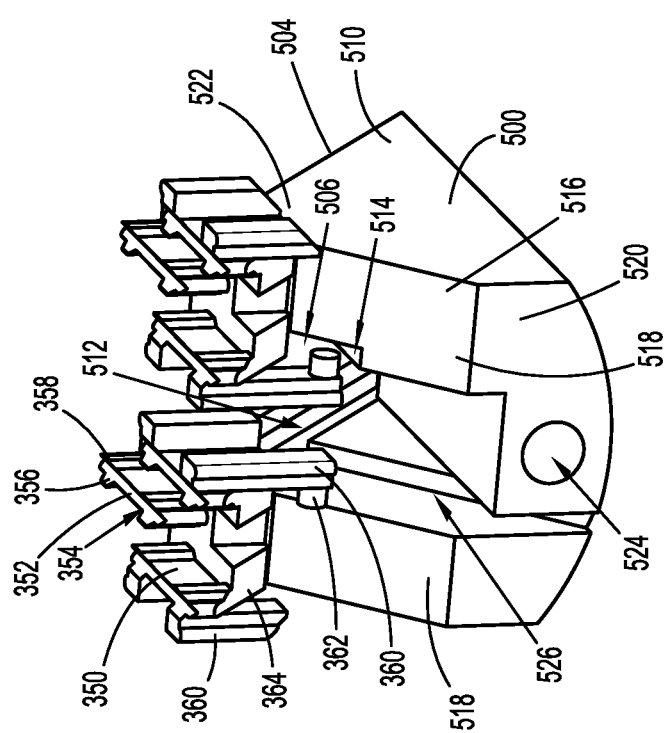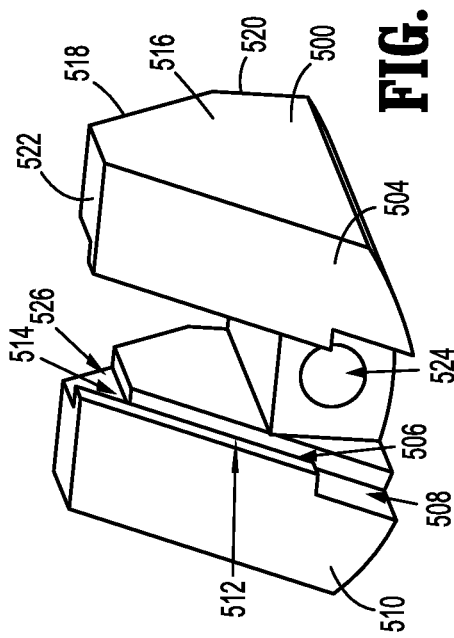
FIG. 7A
FIG. 7B
FIG. 7C

STAPLE FEEDING AND FORMING APPARATUS

CROSS-REFERENCE TO RELATED APPLICATIONS

This application is a continuation of U.S. patent application Ser. No. 15/205,087, filed Aug. 17, 2016, which is a continuation of U.S. patent application Ser. No. 15/204,502, filed Jul. 7, 2016, now U.S. Pat. No. 10,639,033, which is a continuation of U.S. patent application Ser. No. 13/762,511, filed Feb. 8, 2013, now U.S. Pat. No. 9,402,628, which is a continuation of U.S. patent application Ser. No. 13/281,888, filed Oct. 26, 2011, now U.S. Pat. No. 8,418,908, the entire contents of each of which are incorporated by reference herein.

BACKGROUND

Technical Field

The present disclosure relates to surgical staplers. More particularly, the present disclosure relates to a surgical stapling apparatus capable of being reloaded during a surgical procedure without being removed from the surgical site.

Background of the Related Art

Surgical devices for first grasping or clamping tissue between opposing jaw structure and then stapling the tissue with surgical fasteners are well known in the art. In some instruments a knife is provided to cut the tissue which has been stapled by the fasteners. Instruments for this purpose typically include two elongated members, one of which carries a staple cartridge and the other of which includes an anvil. The staple cartridge houses a plurality of staples arranged in at least two lateral rows. The anvil defines a surface for forming the staple legs as the staples are driven from the staple cartridge. In certain devices, the stapling operation is effected by cam bars that travel longitudinally through the staple cartridge. A knife may travel between the staple rows to longitudinally cut and/or open the stapled tissue between the rows of staples.

Often all or part of the stapling assembly of the surgical device is located on a loading unit that is operably connected to a handle assembly. While the handle assembly is configured for multiple uses, the loading unit can be configured for a single use. After the single use is exhausted, the loading unit is removed from the handle assembly and properly disposed.

SUMMARY

Disclosed is a surgical stapling apparatus that includes a loading unit which is capable of being reloaded during a surgical procedure without being removed from the surgical site. This allows a surgeon to continue a surgical operation without withdrawing or removing the surgical stapler for reloading and thus reduces the length of the surgery while allowing the surgeon to concentrate solely on the surgical procedure rather than dividing attention between the surgical procedure and either reloading or replacing the surgical stapler.

An end effector for a surgical stapling apparatus is disclosed including a housing defining a plurality of passageways and a lumen extending longitudinally therethrough. The end effector includes a cartridge which extends from the housing having a channel extending longitudinally therethrough. An upper surface of the channel includes a plurality of retention slots extending therethrough for the reception of surgical fasteners. The end effector also includes an elongate member having a plurality of fasteners arranged in a plurality of longitudinally extending rows where the elongate member is longitudinally translatable through the housing and the cartridge. The elongate member may be made from a flexible material. A plurality of pushers is disposed within the cartridge and are operatively associated with the plurality of retention slots and adapted to support the plurality of fasteners. The end effector also includes a drive member which is movable through the cartridge and adapted to engage the plurality of pushers to urge the plurality of fasteners through the plurality of retention slots. The drive member may include an actuating member extending proximally therefrom which is adapted to move the drive member through the cartridge.

Each of the plurality of pushers may include a post and the drive member may include a slot where the post of each of the plurality of pushers is adapted to engage the slot of the drive member upon actuation of the drive member. Each of the plurality of pushers may include a guide groove and each of the plurality of fasteners may include a corresponding guide portion where the guide portion is adapted to engage the guide groove to guide the fastener when the pusher urges the fastener through one of the plurality of retention slots.

The housing includes an upper housing and a lower housing with the lumen being defined between the upper and lower housings. The passageways of the housing extend from the lumen and are adapted to guide the fasteners through the housing.

The cartridge includes a plurality of grooved channels formed on an underside of the upper surface and aligned with the passageways of the housing. The plurality of grooved channels is laterally aligned with the plurality of retention slots of the upper surface. The plurality of retention slots may include guide surfaces which are adapted for guiding the plurality of surgical fasteners into the plurality of retention slots.

The elongate member defines a plurality of openings arranged in a plurality of longitudinally extending rows where each opening is adapted to receive a fastener and each opening may include perforations where the openings are adapted to tear along the perforations. Each opening may include a pair of holes and a slit and each fastener may include a backspan and a pair of legs extending from the backspan. The backspan of each fastener may be disposed on a first side of the elongate member and the pair of legs of each fastener may extend through the elongate member to a second side of the elongate member.

A surgical stapling apparatus is disclosed including an actuator assembly, a handle supported by the actuator assembly and including an actuation mechanism, an elongated body extending from the actuator assembly and an end effector at the distal end of the elongated body. The end effector includes a housing defining a plurality of passageways and a lumen extending longitudinally therethrough. A cartridge extends from the housing and includes a channel extending longitudinally therethrough. The cartridge includes an upper surface with a plurality of retention slots extending therethrough for the reception of surgical fasteners. An elongate member including a plurality of fasteners arranged in a plurality of longitudinally extending rows is longitudinally translatable through the housing and the cartridge. A plurality of pushers is disposed within the cartridge and is operatively associated with the plurality of retention slots where the plurality of pushers is adapted to support the plurality of fasteners. A drive member is movable through the cartridge and is adapted to engage the plurality of pushers to urge the plurality of fasteners through the plurality of retention slots. The elongate member may be made from a flexible material.

Each fastener may include a backspan and a pair of legs extending from the backspan. The backspan of each fastener may be disposed on a first side of the elongate member and the pair of legs of each fastener may extend through the elongate member to a second side of the elongate member.

The surgical stapling apparatus may further include an anvil assembly including an anvil plate for receiving and forming a fastener. The anvil assembly is in juxtaposed relation to the cartridge and at least one of the anvil assembly and the cartridge is movable in relation to the other of the anvil assembly and the cartridge.

The drive member includes an actuating member extending proximally therefrom which is adapted to move the drive member through the plurality of openings of the cartridge upon actuation of the actuation mechanism.

The elongate member may be adapted to translate through at least a portion of the elongated body.

A method of using a reloadable surgical stapling apparatus during a surgical procedure is disclosed including inserting the surgical stapling apparatus into a surgical site, grasping a first portion of tissue between an anvil assembly and a cartridge assembly of the surgical stapling apparatus, actuating an actuator assembly of the surgical stapling apparatus to drive a first group of fasteners through retention slots of the cartridge assembly and into the first portion of tissue to secure the first group of fasteners to the first portion of tissue, actuating the actuator assembly to release the first portion of tissue and to position a second group of fasteners within the cartridge assembly in substantial alignment with the retention slots, grasping a second portion of tissue between the anvil assembly and cartridge assembly, and actuating the actuator assembly to drive the second group of fasteners through the retention slots and into the second portion of tissue to secure the second group of fasteners to the second portion of tissue.

The method may further include releasing the second portion of tissue and removing the surgical stapling apparatus from the surgical site where the surgical stapling apparatus is removed from the surgical site after at least the first and second groups of fasteners have been secured to the first and second portions of tissue respectively.

Driving one of the first and second groups of fasteners through the retention slots may include translating a drive member at least partially through the cartridge assembly to engage a plurality of pushers disposed in the cartridge assembly and substantially aligned with the retention slots to drive the plurality of pushers towards the retention slots. Driving the plurality of pushers towards the retention slots may include engaging guide surfaces of the plurality of pushers with one of the first and second groups of fasteners to urge the fasteners through the retention slots.

The cartridge assembly may include an elongate member extending therethrough and having the first and second groups of fasteners extending therethrough and arranged in a plurality of longitudinally extending rows. Actuating the actuator assembly to position the second group of fasteners within the cartridge may include translating the elongate member through the cartridge assembly. Urging one of the first and second groups of fasteners through the retention slots may include urging backspans of the fasteners through the elongate member. Translating the elongate member through the cartridge assembly may include translating an empty portion of the elongate member out of the cartridge assembly.

BRIEF DESCRIPTION OF THE DRAWINGS

Various embodiments of the present disclosure are described hereinbelow with references to the drawings, wherein:

FIG. 1A is a perspective view of a surgical stapling apparatus, with portion in phantom, in accordance with the principles of the present disclosure;

FIG. 6A is a perspective view of the pushers and fasteners of FIG. 1A showing guide grooves and guide portions on the pushers and fasteners respectively;

FIG. 6B is an alternate embodiment of the fastener of FIG. 6A;

FIG. 6C is an alternate embodiment of the fastener of FIG. 6A;

FIG. 7A is a front perspective view of the drive member and pusher of FIG. 1A showing the pusher seated on the peak portion;

FIG. 7B is a front perspective view of FIG. 7A showing the pushers with the posts engaging the channel of the drive member as the pushers translate up the ramp;

FIG. 7C is a rear perspective view of FIG. 7A showing only the drive member;

DETAILED DESCRIPTION OF THE EMBODIMENTS

Figure 1B:
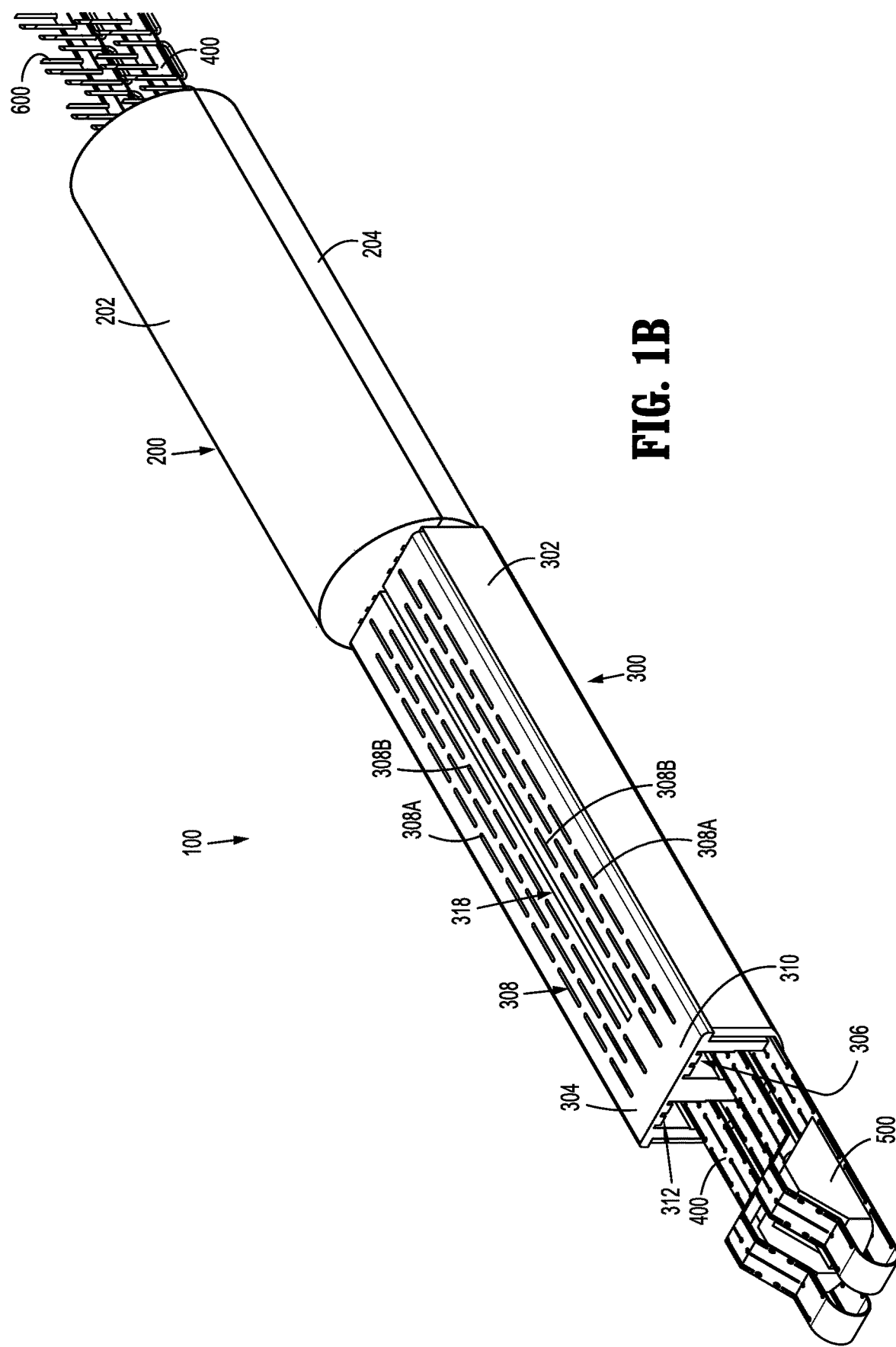
FIG. 1B is a perspective view of the distal portion of the surgical stapling apparatus of FIG. 1A.

In the drawings and in the description which follows, in which like references numerals identify similar or identical elements, the term "proximal" will refer to the end of the apparatus which is closest to the clinician during use, while the term "distal" will refer to the end which is furthest from the clinician, as is traditional and known in the art.

FIG. 1A illustrates a surgical stapling apparatus 10 including an embodiment of an end effector according to the present disclosure shown generally as end effector 100. As shown in FIG. 1A, and as will be discussed hereinbelow, end effector 100 is configured for attachment to an actuator assembly 12 to form surgical stapler 10. Actuator assembly 12 includes a handle assembly 20 and an elongated body 30 extending from handle assembly 20. Elongated body 30 is configured for use in closed procedures, i.e., laparoscopic, endoscopic, arthroscopic, however, elongated body 30 may be shortened or eliminated for use in open procedures. In the present disclosure, actuator assembly 12 will only be described to the extent necessary to fully disclose end effector 100. For a more detailed description of the structure and function of a surgical stapler similar to actuator assembly 12, please refer to commonly owned U.S. Pat. No. 5,865,361 to Milliman et al. ("Milliman '361 patent"), the contents of which is incorporated herein in by reference in its entirety.

Referring to FIGS. 1A and 1B, end effector 100 includes an anvil assembly 110, a housing 200, a cartridge assembly 300, an elongate member 400, and a drive member 500. Anvil assembly 110 includes fastener deforming depressions 112 (FIG. 19) for deforming fasteners to secure tissue "T".

As seen in FIGS. 2A-2E, housing 200 defines an elongate shape and includes an upper housing 202 and a lower housing 204 which define a gap or lumen 206 therebetween extending longitudinally through housing 200. Housing 200 also includes a plurality of passageways 208 extending from lumen 206 into upper housing 202 and extending longitudinally through upper housing 202. Lower housing 204 defines longitudinally extending grooves 210 extending from lumen 206 into lower housing 204 and laterally aligned with passageways 208. Housing 200 may also include an actuation channel 212 for receiving an actuation mechanism 502 (FIG. 5A) therethrough. Actuation mechanism 502 may be used for actuating drive member 500. Actuation channel 212 may, for example, be disposed in the lower housing 204.

Figure 19:
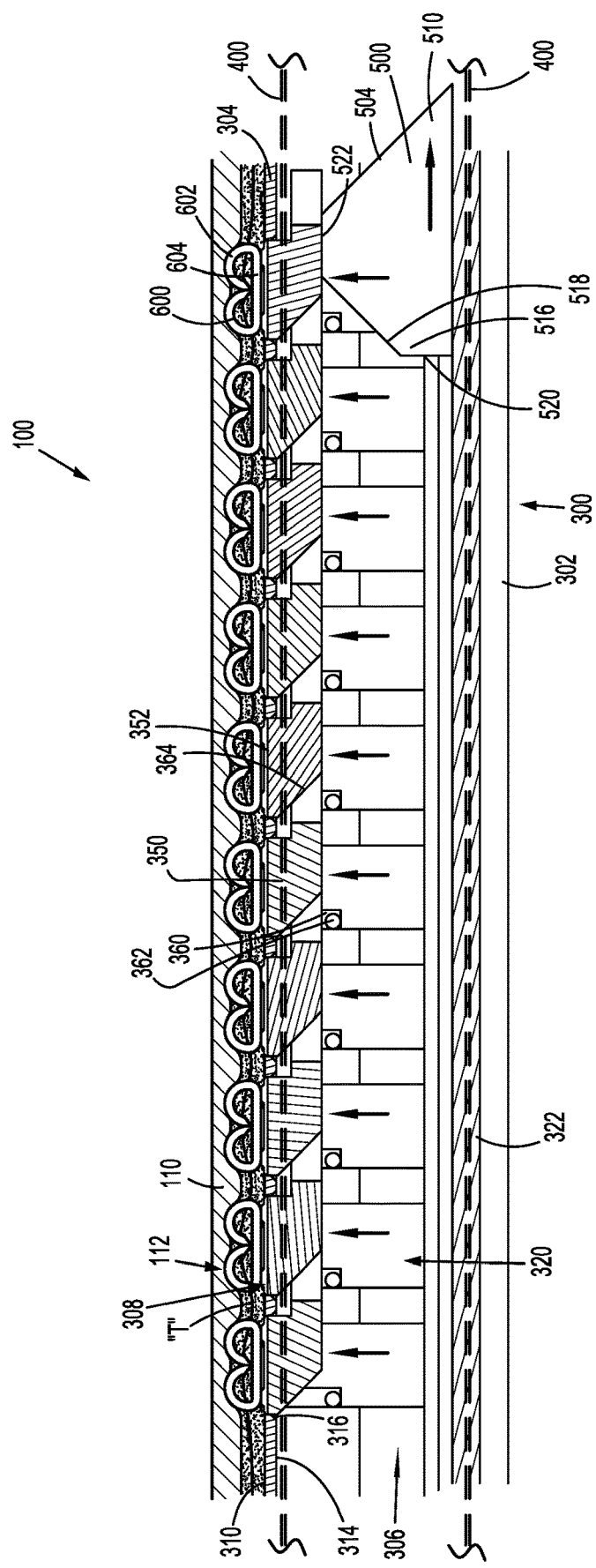
FIG. 19 is a side cross-sectional view of the end effector of the surgical stapling apparatus of FIG. 1A after the drive member has been translated to the fully fired position.

Referring now to FIGS. 3A-3D, cartridge assembly 300 extends from housing 200 and includes a casing 302 dimensioned and configured to receive a cartridge 304. Cartridge 304 includes a plurality of spaced apart channels 306 extending longitudinally therethrough. Cartridge 304 also includes a plurality of retention slots 308 extending through an upper surface 310 of cartridge 304 and aligned with the plurality of fastener deforming depressions 112 of the anvil assembly 110 (FIG. 19). Plurality of retention slots 308 may define a plurality of rows and each row may be associated with one of the plurality of spaced apart channels 306. For example, each channel 306 may include an outer row of retention slots 308A and an inner row of retention slots 308B. A knife slot 318 may be disposed between adjacent channels 306 for receiving a knife blade (not shown) therethrough. Each channel 306 may also include additional rows of retention slots 308 as desired, where, for example, each channel 306 may include three or more rows of retention slots 308 or each channel 306 may include only a single row of retention slots 308.

Cartridge 304 also includes a plurality of grooved channels 312 extending longitudinally along an underside 314 of the upper surface 310 of cartridge 304. Plurality of grooved channels 312 are each laterally aligned with one of the rows of retention slots 308. As seen in FIGS. 4A-4E, retention slots 308 may also include guide surfaces 316 on underside 314 of upper surface 310. Guide surfaces 316 may, for example, be chamfered, angled, radial, or other types of contoured surfaces suitable to guiding fasteners through retention slots 308. Cartridge 304 also includes a plurality of pushers 350 operatively associated with retention slots 308, as will be described in more detail below.

Figure 2A:
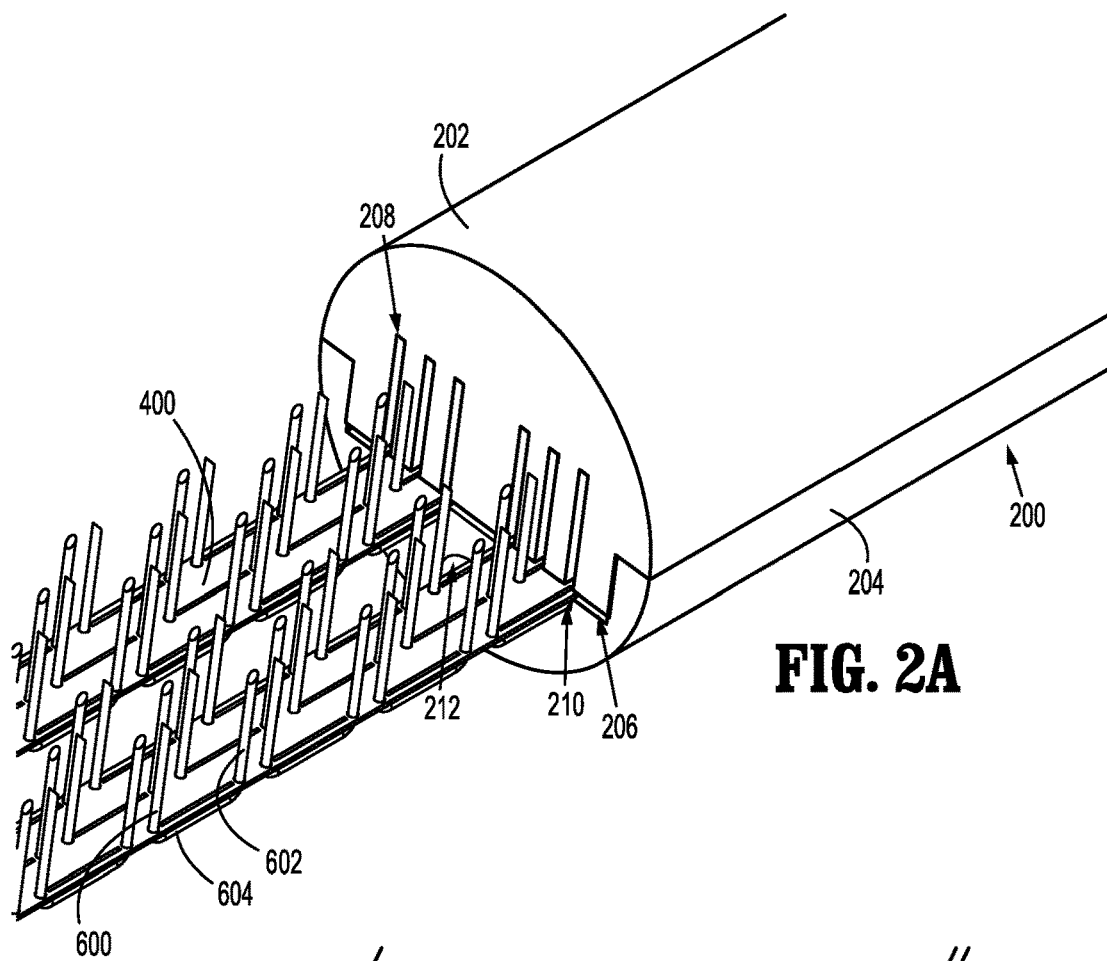
FIG. 2A is a perspective view of the housing of the surgical stapling apparatus of FIG. 1 showing the elongate member and fasteners extending out of the housing.
Figure 2B:
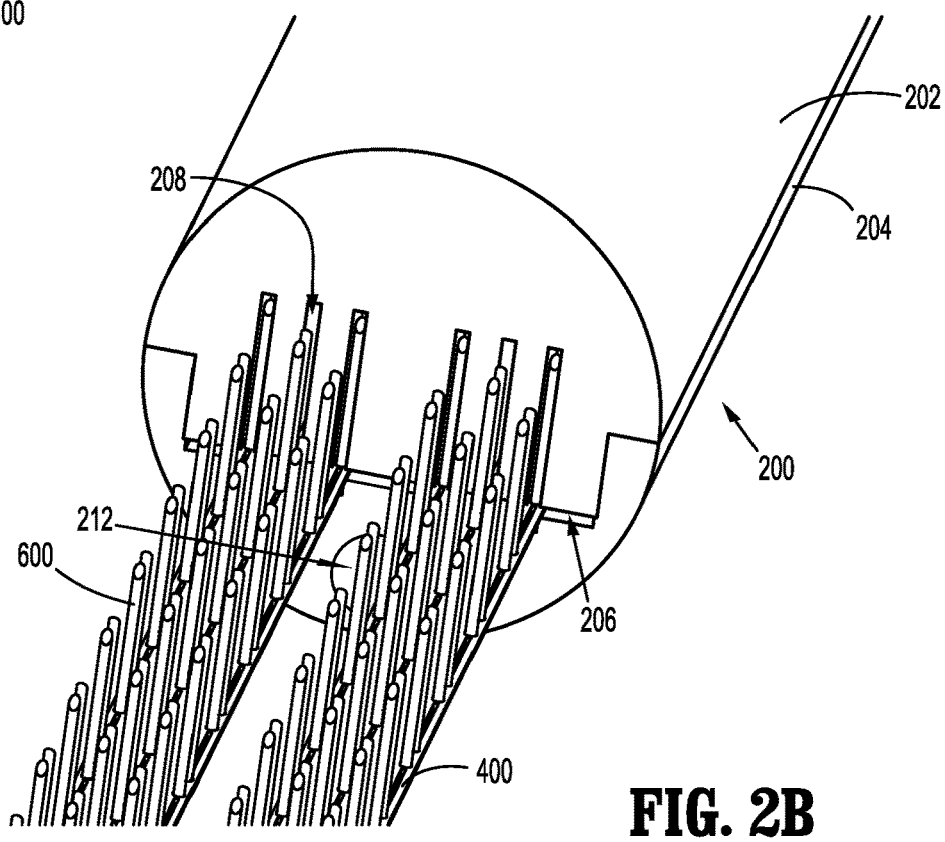
FIG. 2B is a front perspective view of the housing of FIG. 2A.
Figure 2C:
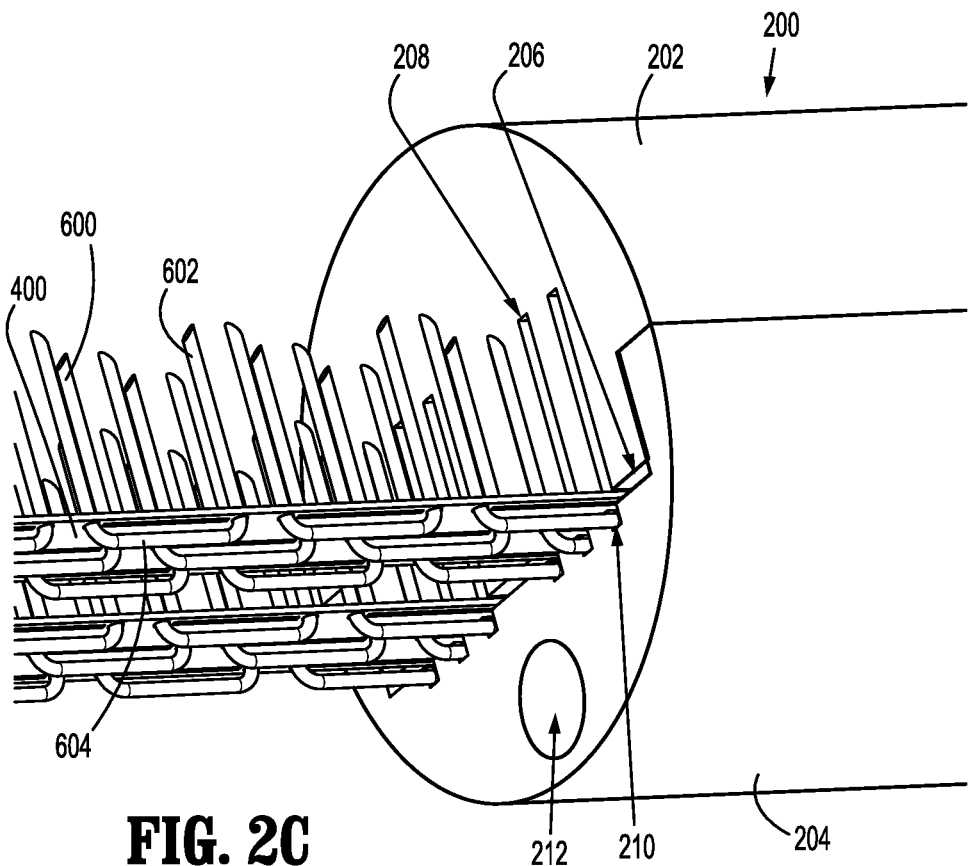
FIG. 2C is a side perspective view of the housing of FIG. 2A.
Figure 2D:
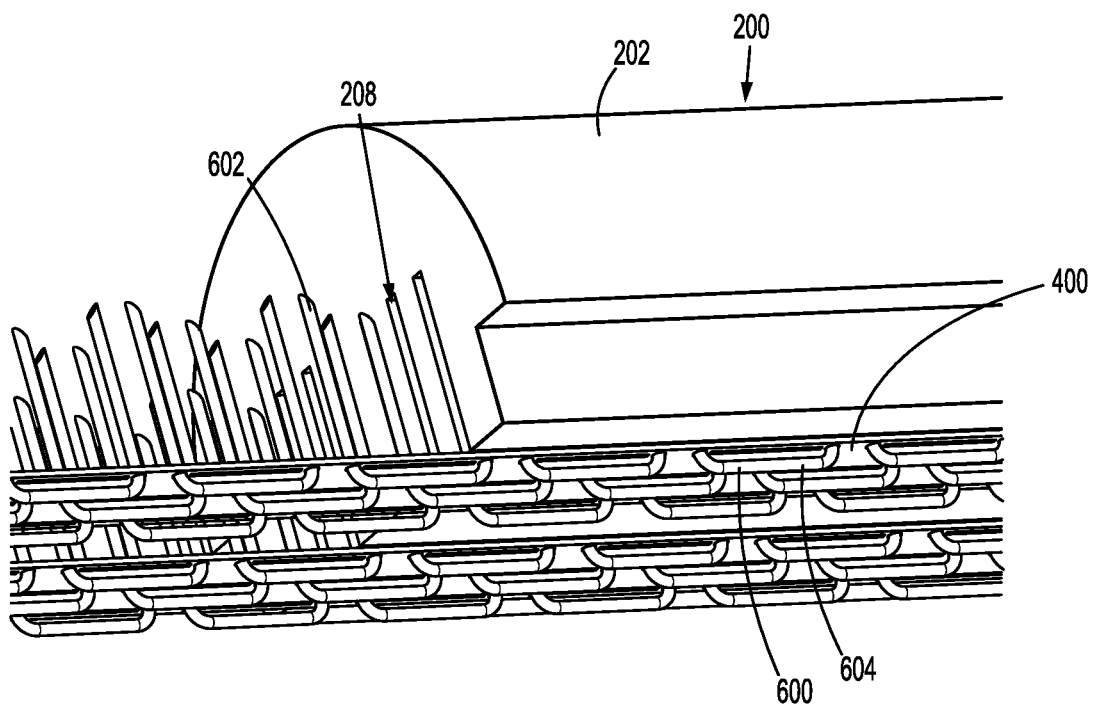
FIG. 2D is a side perspective of FIG. 2C with the lower housing removed.
Figure 2E:
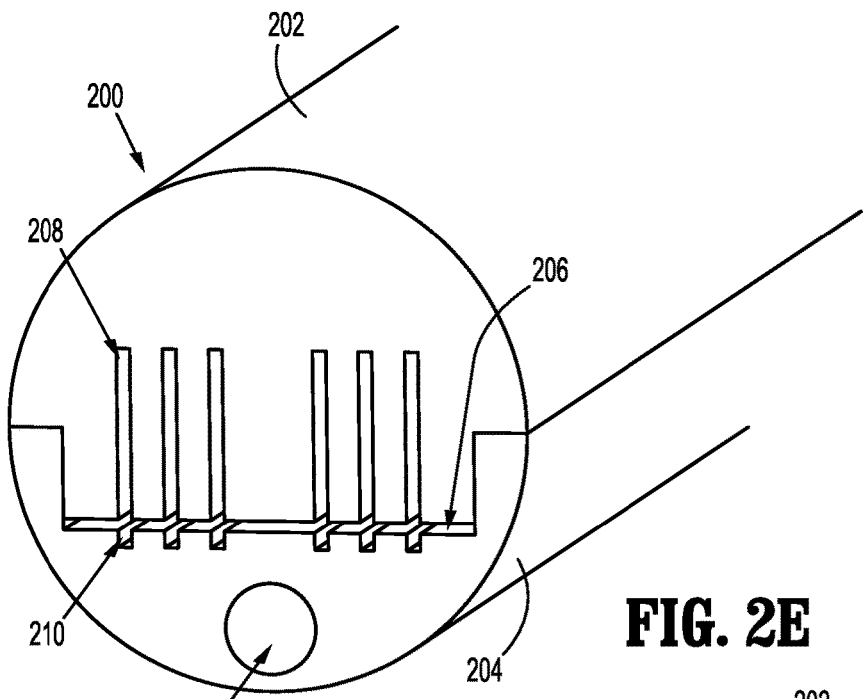
FIG. 2E is a front perspective view of FIG. 2B. with the elongate member and fasteners removed.
Figure 3A:
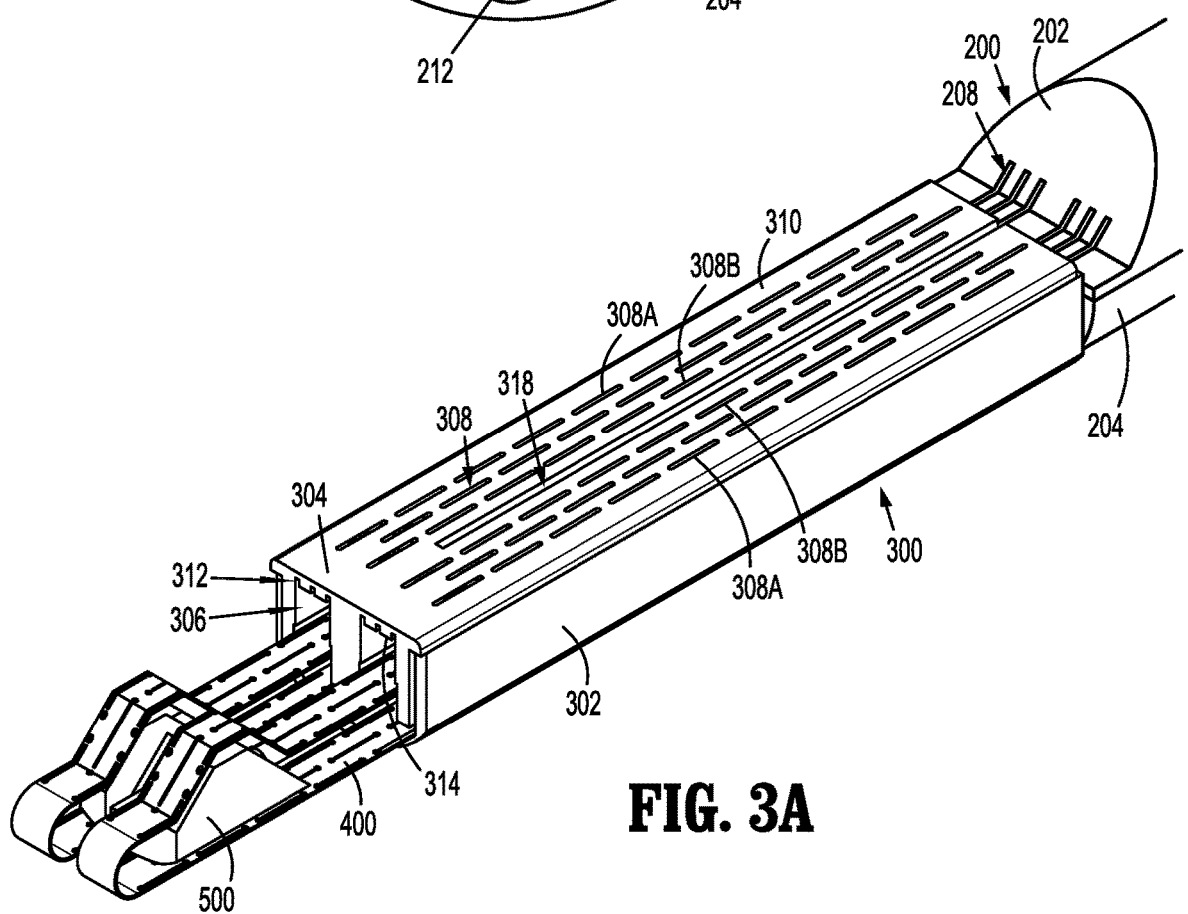
FIG. 3A is a perspective view of the distal portion of the surgical stapling apparatus of FIG. 1A.
Figure 3B:
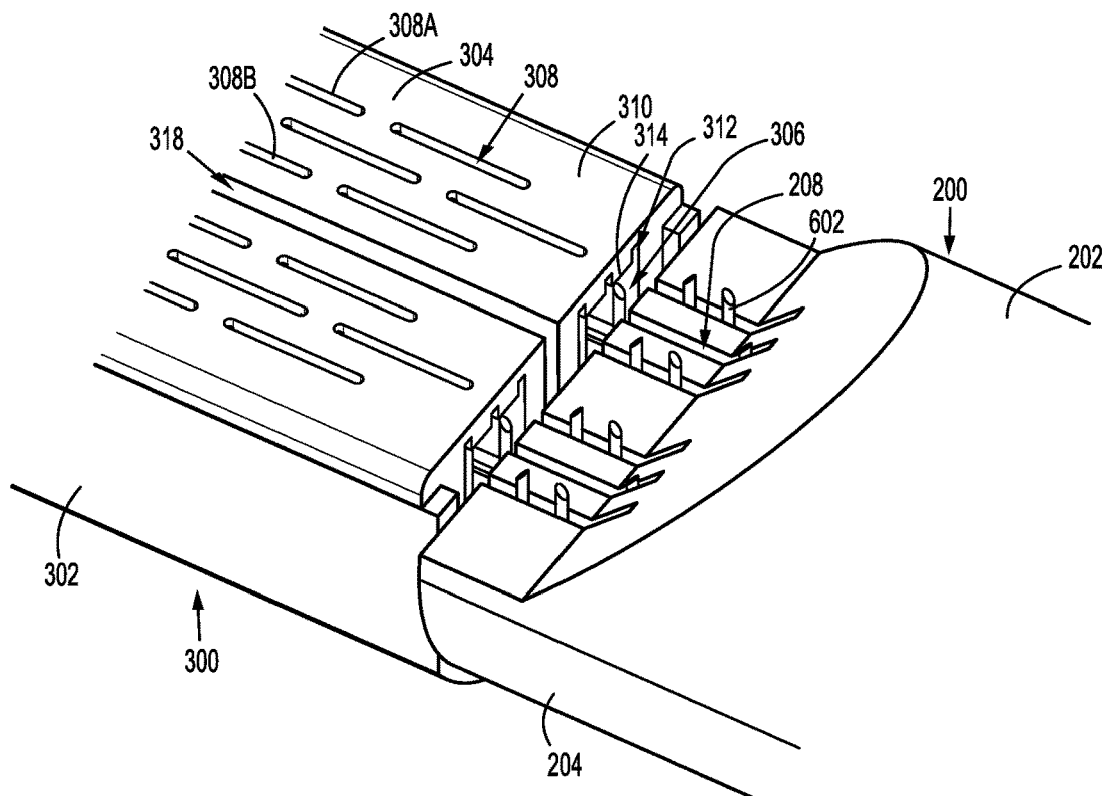
FIG. 3B is a perspective view of the juncture between the housing and the cartridge assembly of FIG. 3A.
Figure 3C:
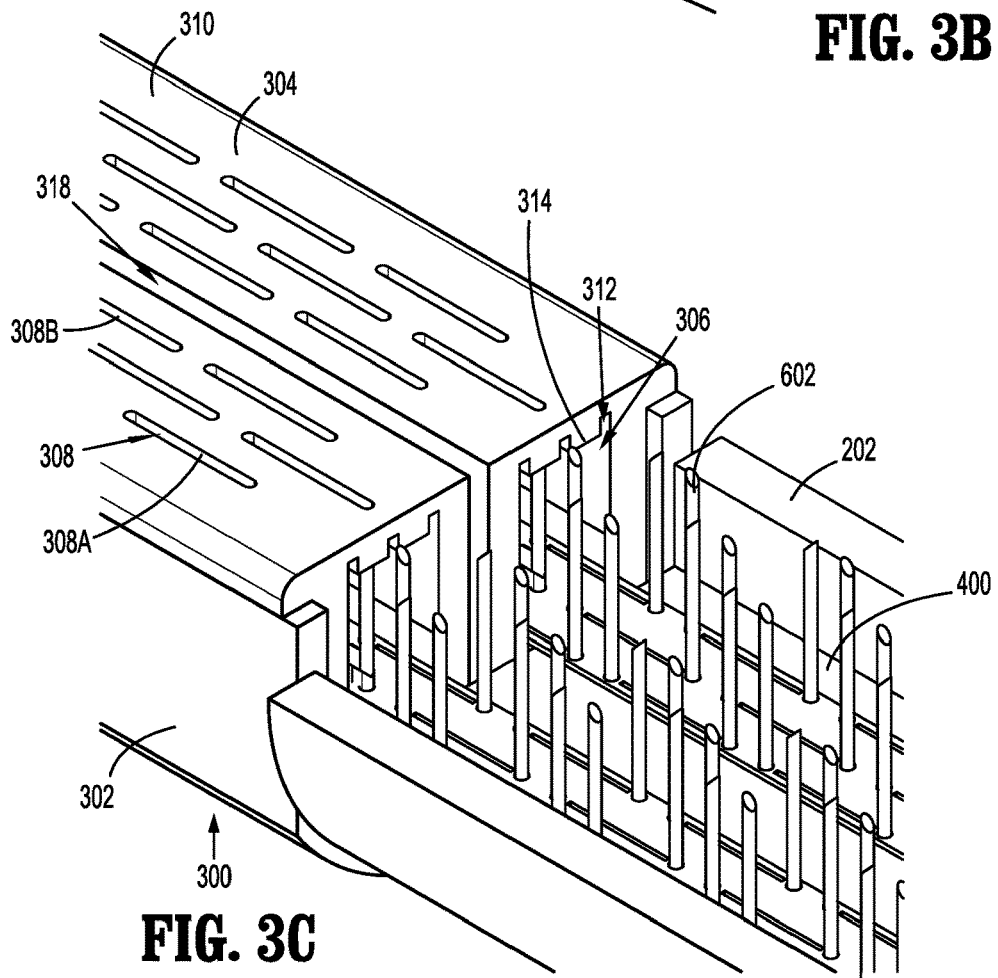
FIG. 3C is a perspective view of FIG. 3B with the upper housing removed.
Figure 3D:
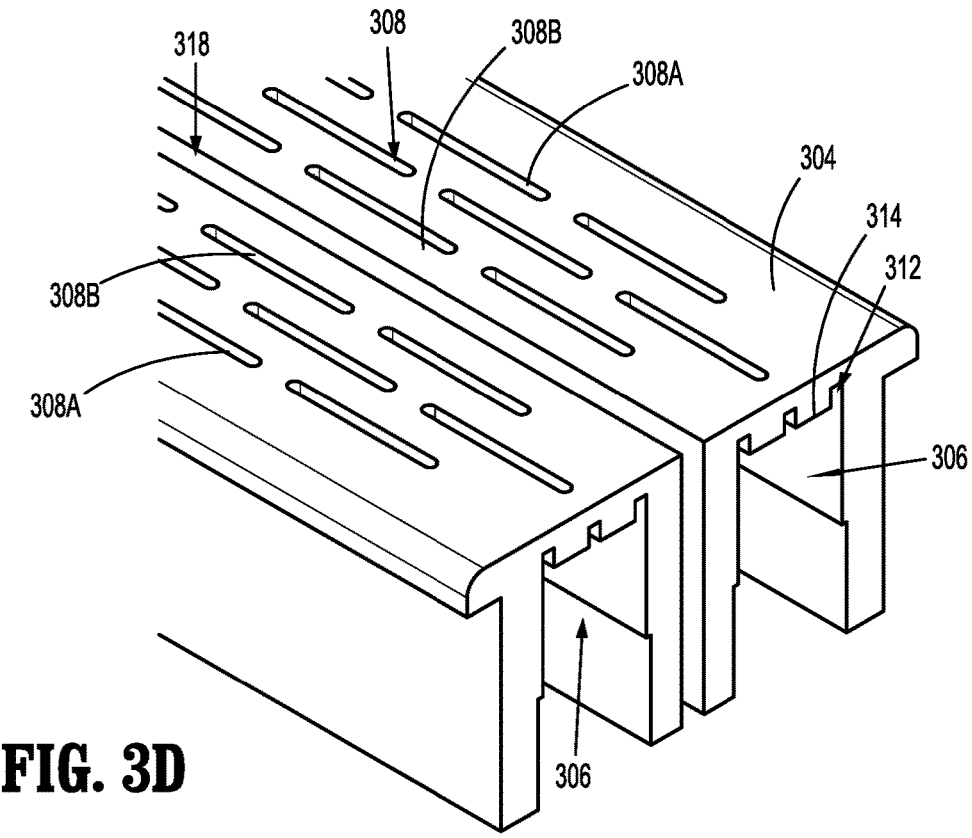
FIG. 3D is a perspective view of the cartridge of FIG. 3A.
Figure 4A:
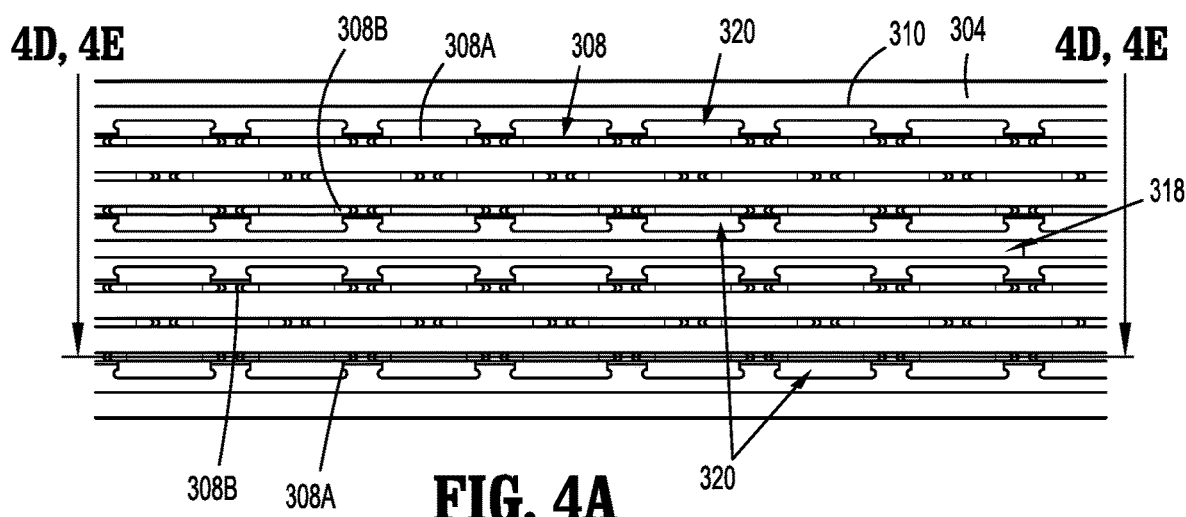
FIG. 4A is top plan view of the cartridge of FIG. 1A.
Figure 4B:
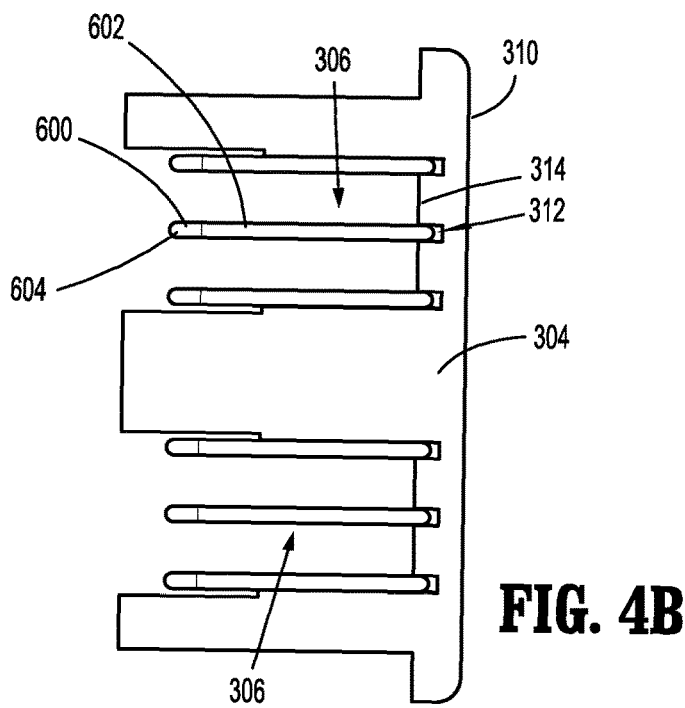
FIG. 4B is an end view of FIG. 4A showing the fasteners disposed in the grooved channels.
Figure 4C:
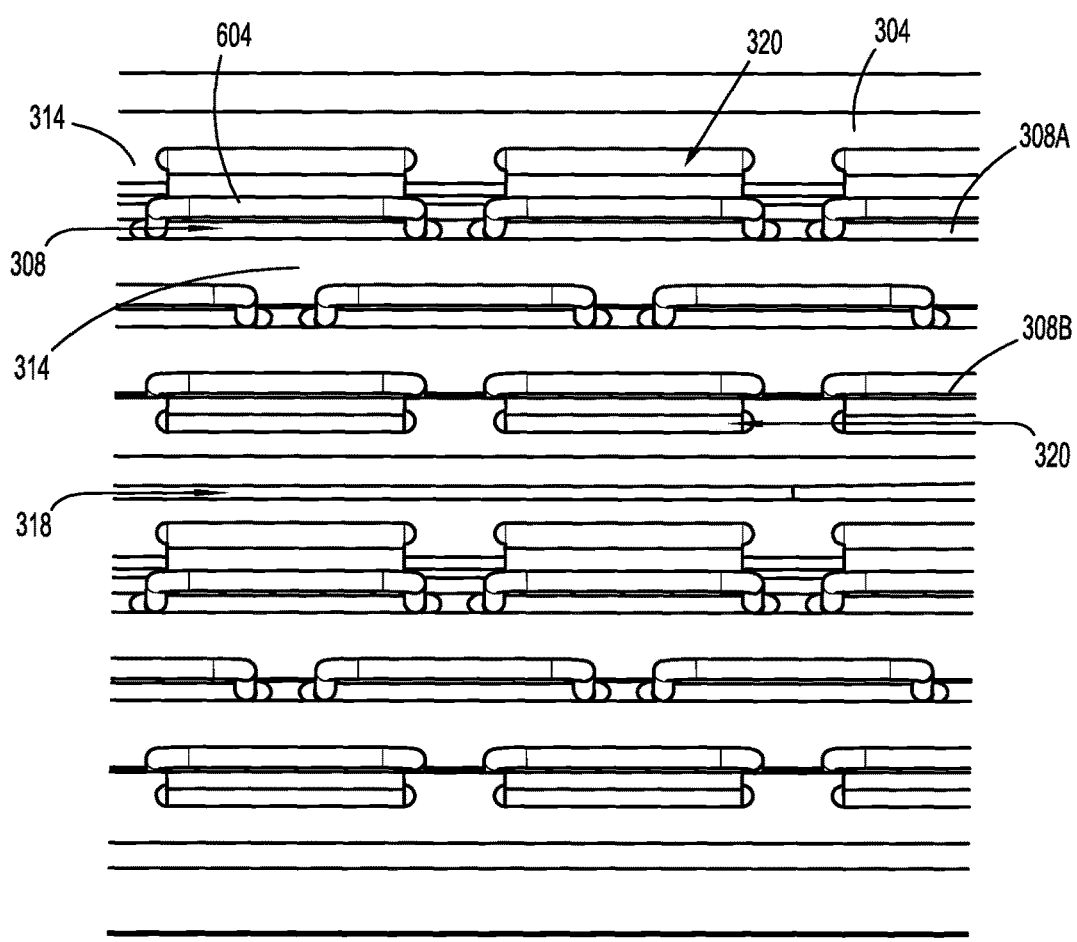
FIG. 4C is a bottom plan view of FIG. 4B.
Figure 4D:
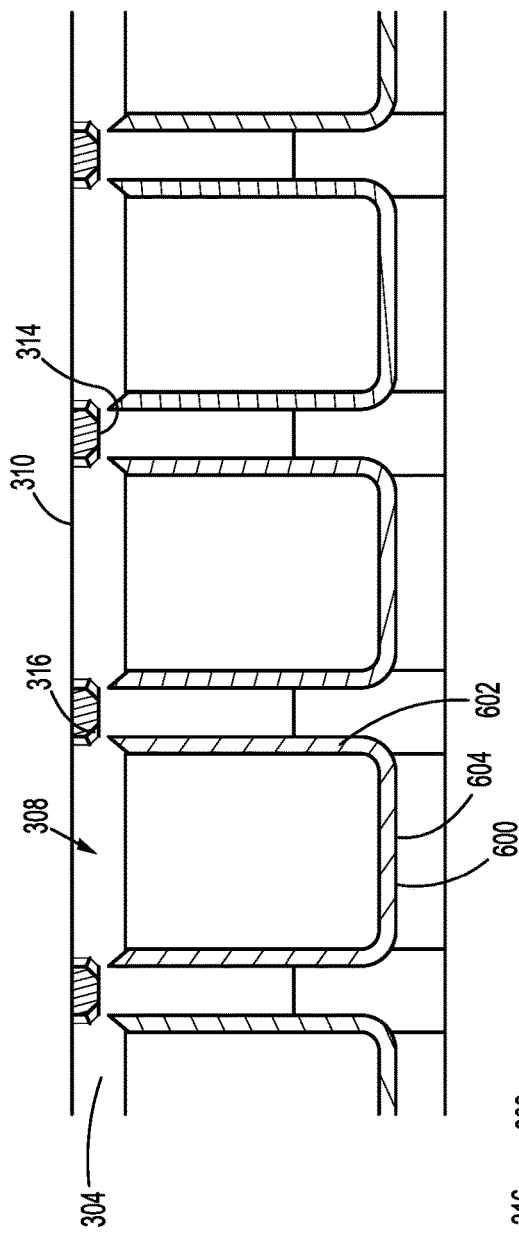
FIG. 4D is a side cross-sectional view of FIG. 4A.
Figure 4E:
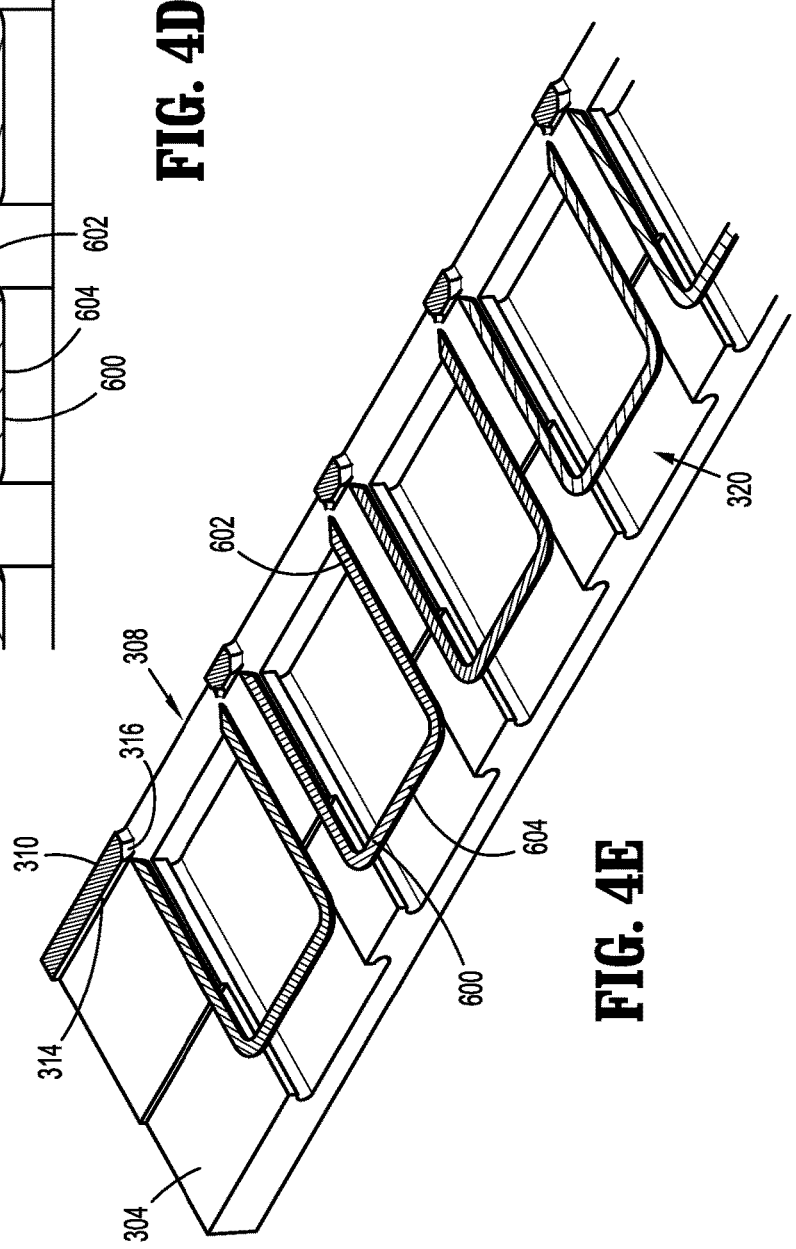
FIG. 4E is a perspective cross-sectional view of FIG. 4D.
Figure 5A:
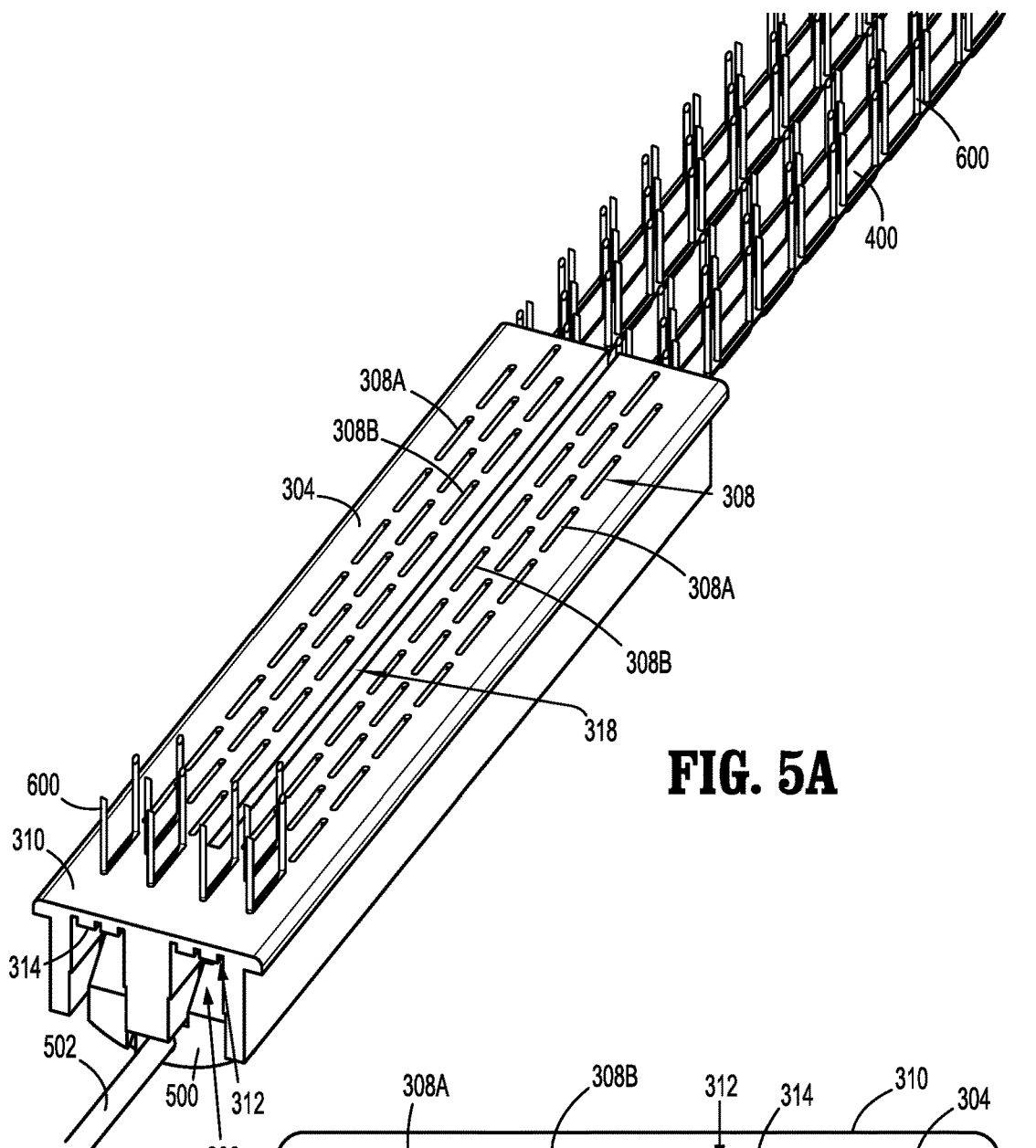
FIG. 5A is a front perspective view of the cartridge assembly of FIG. 1A showing the drive member translating through the cartridge to drive the fasteners through the retention slots.
Figure 5B:
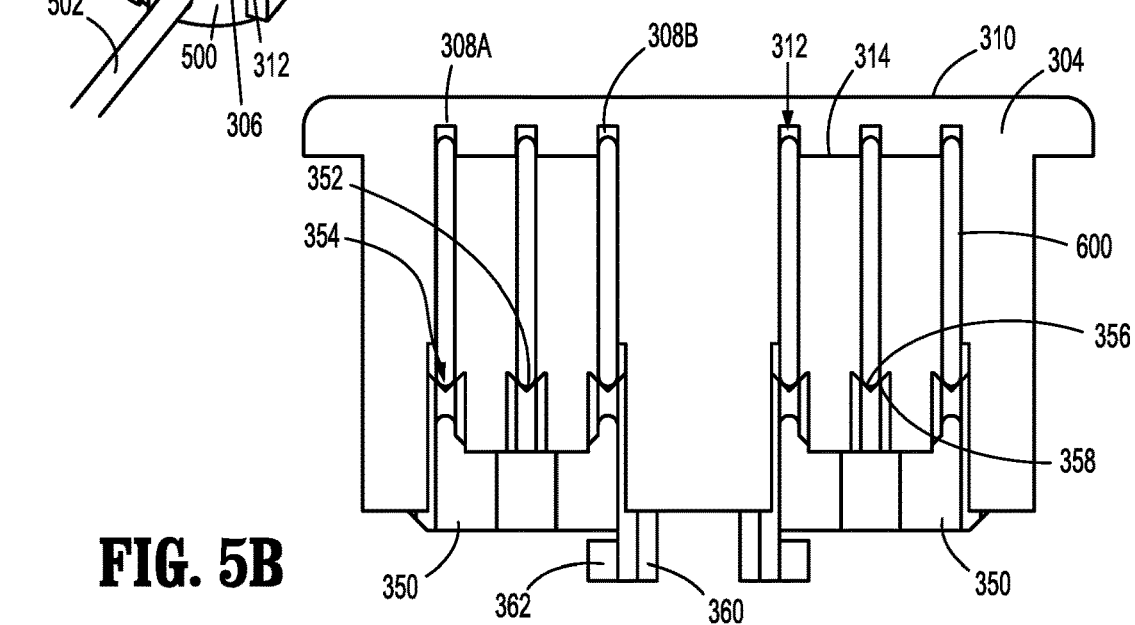
FIG. 5B is an end view of FIG. 5A.
Figure 5C:
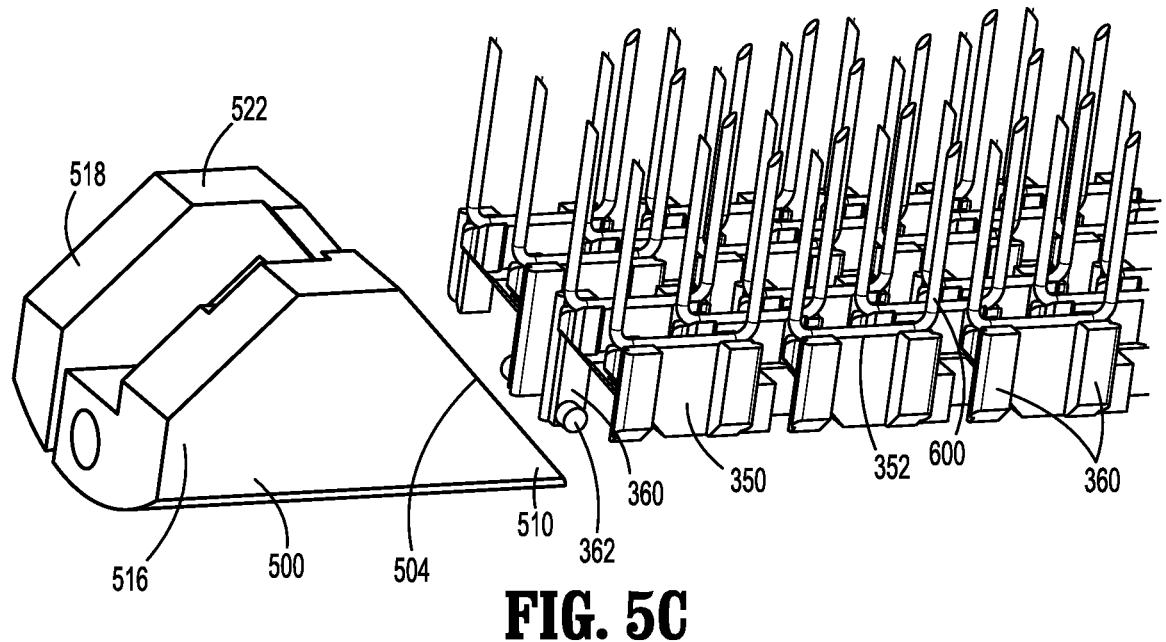
FIG. 5C is a perspective view of the drive member, pushers and fasteners of FIG. 5A.
Figure 5D:
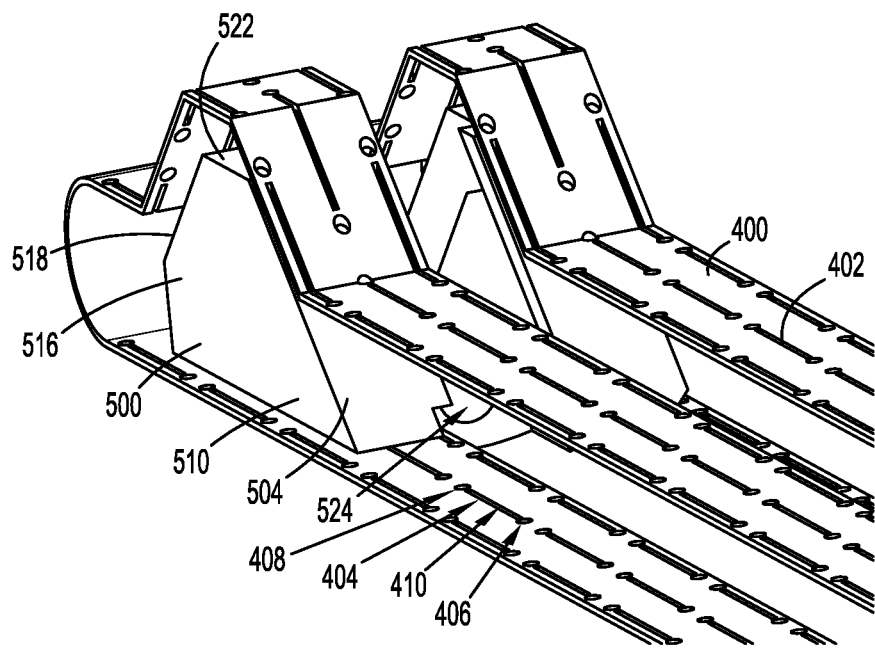
FIG. 5D is a perspective view of the drive member and elongate member of FIG. 5A.
Figure 5E:
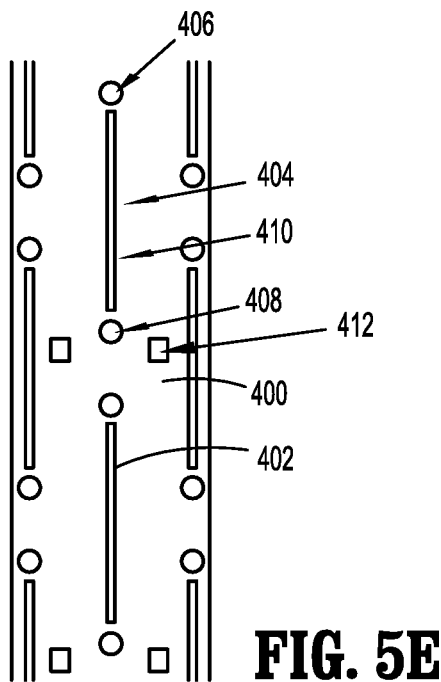
FIG. 5E is a top plan view of the elongate member of FIG. 5A.
Figure 5F:
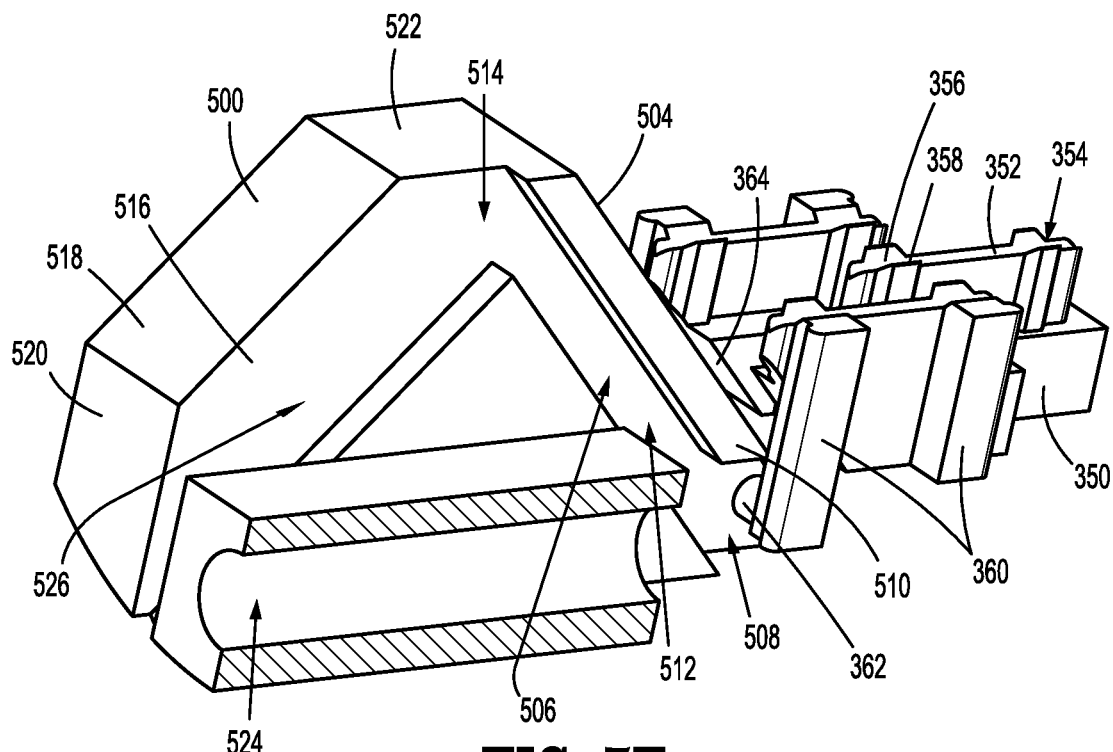
FIG. 5F is a side perspective view, partially in section, of the drive member and pushers of FIG. 5A.
Figure 5G:
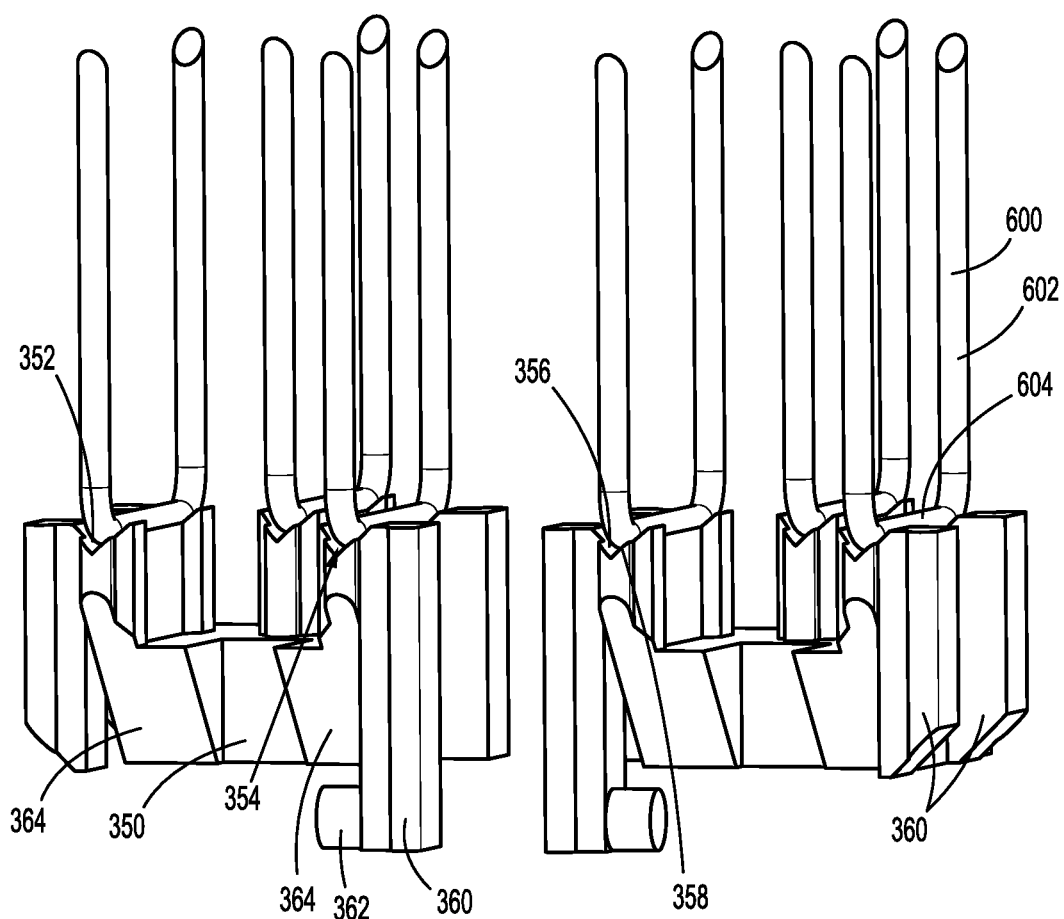
FIG. 5G is a front perspective view of the pushers of FIG. 5A with fasteners resting in the guide grooves.
Figure 8:
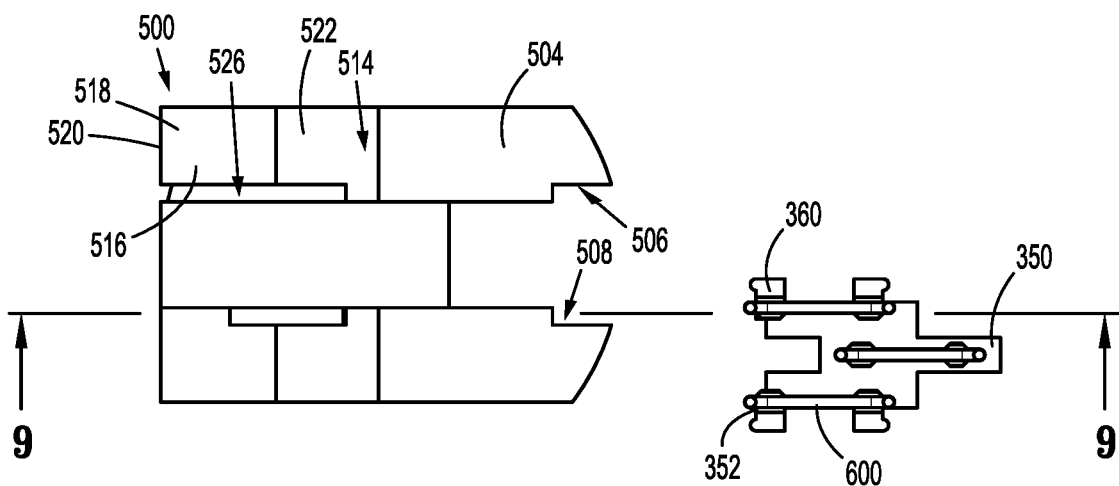
FIG. 8 is a top view of the drive member and pusher of FIG. 1A.

Referring now to FIGS. 2A-2D, 3B-3C, 5A, 5D, and 5E, elongate member 400 includes a plurality of fasteners 600 extending therethrough and arranged in a plurality of longitudinally extending rows 402. Each of rows 402 may correspond to and align with one of the rows of retention slots 308 and additional elongate members 400 may be included where, for example, each channel 306 of cartridge 304 receives an elongate member 400. Each fastener 600 includes a pair of legs 602 and a backspan 604 (FIGS. 4D-4E) where each backspan 604 is disposed on a first side of elongate member 400 and each pair of legs 602 extend through elongate member 400 to a second side. Elongate member 400 and fasteners 600 are longitudinally translatable through housing 200 where lumen 206 of housing 200 is adapted to receive elongate member 400 and passageways 208 and grooves 212 are adapted to receive legs 602 and backspan 604 of fasteners 600 respectively (FIGS. 2B and 2C). Passageways 208 and grooves 212 are adapted to guide fasteners 600 through housing 200 as elongate member 400 translates longitudinally through housing 200. Elongate member 400 and fasteners 600 are also longitudinally translatable through the housing and cartridge assembly 300 to move the fasteners from a position proximal of the retention slots to a position in line with the slots. Channels 306 are adapted to receive elongate member 400 and fasteners 600, while grooved channels 312 engage at least a portion of legs 602 of fasteners 600 to maintain the lateral position of fasteners 600 relative to retention slots 308 (FIGS. 3B, 3C, and 4B). Elongate member 400 may be made of a flexible or deformable material such as, for example, a rubber, a cotton or other cloth, fabric, or textile, a plastic web or mesh, a plastic compound, silicone, gum rubber, or any other material suitably flexible and adaptable for translation through housing 200 and cartridge assembly 300 to allow fasteners 600 to be fired by pushers 350. Elongate member 400 includes openings 404 therethrough for the reception of fasteners 600. Each opening 404 may include, for example, a pair of holes 406 and 408 and a slit 410 extending at least partially therebetween, as seen in FIG. 5E. Each pair of legs 602 of fasteners 600 extends through pair of holes 406 and 408 respectively and each backspan 604 is substantially aligned with one of slits 410.

Referring now to FIGS. 5F-5G, 6A-6C, and 7A-7C, pushers 350 include a plurality of pushing surfaces 352 for engaging fasteners 600 and pushing surfaces 352 may define guide grooves 354 for engaging backspans 604 and guide portions 606 of fasteners 600. Guide portions 606 may be defined by backspans 604 or may be in addition to backspans 604 (FIGS. 6A-6C). Guide grooves 354 are configured to maintain the alignment of fasteners 600 relative to retention slots 308 and to assist in guiding and stabilizing fasteners 600 as they move through retention slots 308. Guide grooves 354 may, for example, include sloped surfaces 356 and 358 (FIG. 6A) for centering backspans 604 of fasteners 600 within guide grooves 354 and may define a shape corresponding to guide portions 606 for receiving and engaging guide portions 606 and backspans 604. Sloped surfaces 356 and 358 may, for example, be any angled, radial, or contoured surface suitable to provide lateral support to fasteners 600 and assist in positioning or centering fasteners 600 during firing. Pushers 350 also include flanged portions 360 for engaging alignment slots 320 of cartridge assembly 300 and guiding pushers 350 toward retention slots 308. Pushers 350 may also include posts or protrusions 362 (FIG. 5G) for engaging drive member 500.

Referring now to FIGS. 1B, 5A, 5C, 5D, 5F, 7A-7C, and 8-19, drive member 500 is longitudinally translatable through cartridge assembly 300 (FIG. 5A) between an initial position at a distal portion of cartridge assembly 300 (FIG. 1B) and a fully fired position at a proximal portion of the cartridge assembly 300 (FIG. 19). It is also contemplated that the initial position may be at a proximal portion of cartridge assembly 300 and the fully fired position may be at a distal portion of cartridge assembly 300 where drive member 500 translates distally from the initial position to the fully fired position. Drive member 500 may optionally be only partially translated through cartridge assembly 300 such that only a portion of fasteners 600 is fired.

Figure 9:
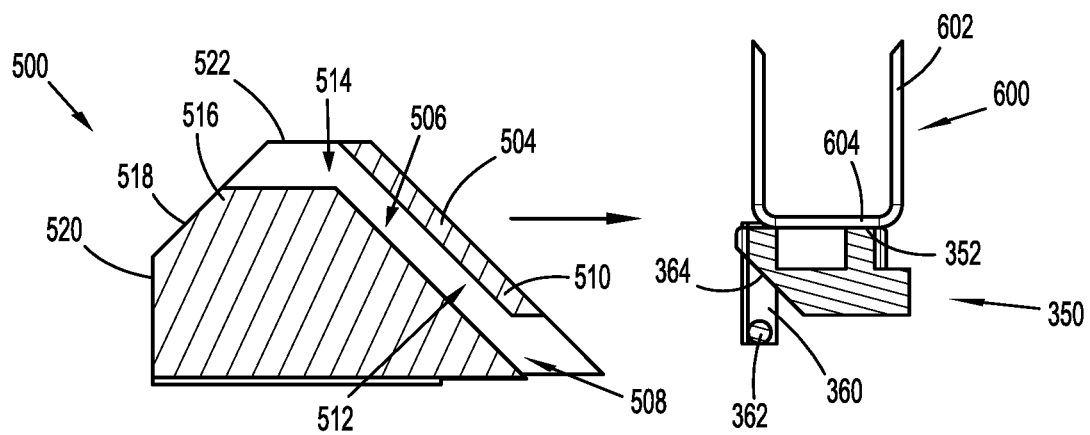
FIG. 9 is a side cross-sectional view of the sled and pusher of FIG. 8, taken along section line 9-9, prior to the drive member engaging the pusher.
Figure 10:
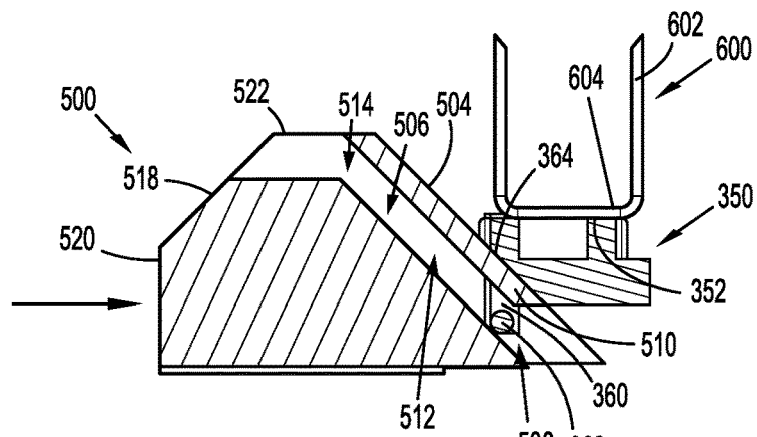
FIG. 10 is a view of FIG. 9 showing the post of the pusher engaging the channel of the drive member at the inlet opening.
Figure 11:
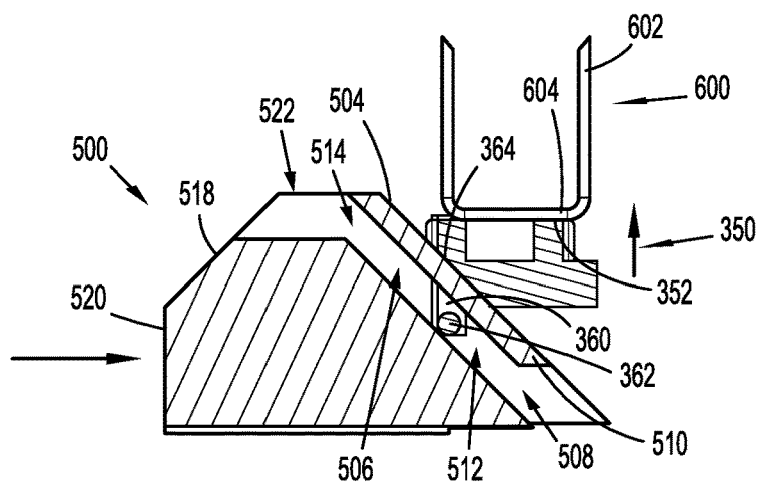
FIG. 11 is a view of FIG. 10 showing the pusher translating up the ramp of the drive member.
Figure 12:
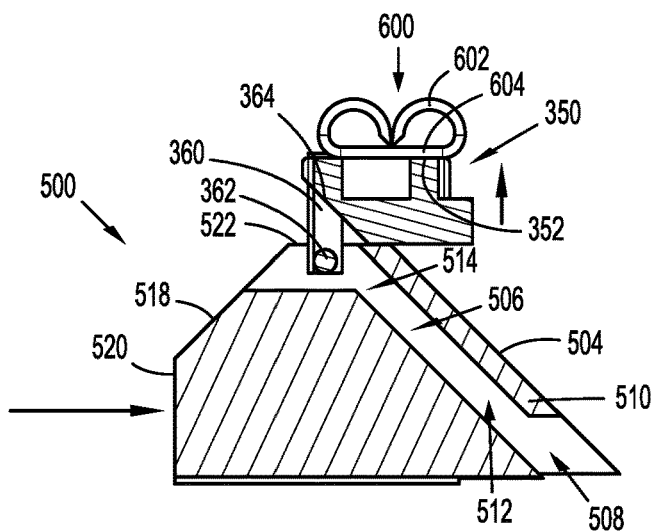
FIG. 12 is a view of FIG. 11 showing the pusher at the peak portion of the drive member with the fastener having been formed.

Drive member 500 is operatively associated with plurality of pushers 350 such that as drive member 500 translates through cartridge assembly 300, drive member 500 engages each of pushers 350 with ramps 504 (FIGS. 9-12). Pushers 350 translate along ramps 504 to urge fasteners 600 through retention slots 308. Pushers 350 may also include distal sloped surfaces 364 for engaging ramps 504 during translation of drive member 500 from the initial position toward the fully fired position (FIGS. 10-12).

Drive member 500 may include slots 506 for receiving posts 362 of pushers 350 and posts 362 may be substantially cylindrical or curved to facilitate entry into slots 506. Alternatively posts 362 maybe any shape suitable for entry into slots 506 to provide a camming action with slots 506 including, for example, linear shapes, squares, triangles, oblong shapes, or other polygonal or curved shapes. Slots 506 each define an inlet opening 508 at a leading or proximal portion 510 of drive member 500, a channel 512 extending substantially parallel to ramp 504 for translation of posts 362 therethrough, and an outlet opening 514 at a trailing or distal portion 516 of drive member 500, as seen in FIGS. 9-18. Trailing portion 516 may also include ramps 518 and outlet openings 514 may be defined at a peak portion 522 of drive member 500 or may be defined at the trailing edge 520 of ramps 518. Pushers 350 may include proximal sloped surfaces (not shown) for engaging ramp 518 during translation of drive member 500 from the fully fired position (FIG. 19) toward the initial position (FIG. 1B). Channel 512 may further include a distal portion 526 (FIG. 5F) extending through drive member 500 parallel to ramp 518 for receiving posts 362. In alternative embodiments, no posts 362 or slots 506 are included for use with pushers 350 where, for example, pushers 350 engage ramps 504 without the support of posts 362 and slots 506.

Referring now to FIGS. 2D, 5A, 5F, and 7A-7C, drive member 500 translates through cartridge assembly 300 by actuation of actuation mechanism 502 (FIG. 5A). Actuation mechanism 502 is operatively associated with actuator assembly 12 and is coupled to drive member 500. Actuation mechanism 502 extends from actuator assembly 12 through actuation channel 212 of housing 200, cartridge assembly 300, and a lumen 524 of drive member 500. Lumen 524 extends through drive member 500 and is adapted for the reception of actuation mechanism 502. Lumen 524 may, for example, include an internal thread for engaging actuation mechanism 502. Actuation mechanism 502 may be in the form of a screw, a rod or other mechanism suitable to translate drive member 500 through cartridge assembly 300.

Actuator assembly 12 may be adapted to independently translate elongate member 400 through housing 200 and cartridge assembly 300 through the use of an actuator (not shown) such as, for example, a spool, a gear system or another suitable mechanism for advancing elongate member 400 through housing 200 and cartridge assembly 300. The actuator may directly contact elongate member 400 or may instead drive a pulley system to translate elongate member 400 through housing 200 and cartridge assembly 300. Elongate member 400 may be wound around a pulley or other suitable mechanism at the distal end of end effector 100 and may return to housing 200 via cartridge 300. For example, elongate member 400 may return through channels 306 of cartridge 300 to lumen 206 of housing 200. Alternatively a separate pathway 322 (FIG. 19) may be defined by both cartridge 300 and housing 200 for receiving the used portion of elongate member 400.

Elongate member 400 may, for example, include a feed mechanism 412 (FIG. 5E) such as a slot or cut-out which is engagable by a gear or spool mechanism to advance elongate member 400 through housing 200 and cartridge assembly 300. The actuator may also be configured to cooperate with drive member 500 after firing to return drive member 500 to the initial position at the distal end of end effector 100 while re-loading cartridge 300 with a new set of fasteners 600. Alternatively, drive member 500 may include hooked portions (not shown) for engaging feed mechanism 412 as drive member 500 returns to the initial position after firing where, for example, the hooked portions are angled at least partially in the distal direction such that as drive member 500 translates proximally feed mechanism 412 is not engaged with the hooked portions but when drive member 500 translates distally the hooked portions engage feed mechanism 412 and translate elongate member 400 distally by the same amount as drive member 500. This allows cartridge assembly 300 to be reloaded through the single action of resetting or translating drive member 500 to the initial position and in addition allows a surgeon to at least partially reload cartridge assembly 300 during use. For example, if only a portion of the fasteners within cartridge assembly 300 were fired the surgeon may reset drive member 500 to the initial position to fully reload the cartridge assembly 300 by the number of fasteners which were already fired without disposing of the remaining fasteners. In addition the surgeon may, for example, perform a partial reloading of the cartridge assembly 300 by translating drive member 500 only a part of the way to the initial position after firing. This allows the surgeon to utilize variable reloading as needed during a surgical procedure without having to dispose of or replace the cartridge assembly Housing 200 may include a pre-determined number of fasteners 600 for feeding into cartridge assembly 300 where, for example, a number of reloads or groups of fasteners 600 may be provided to allow a surgeon to reload and fire surgical stapling apparatus 10 multiple times without removing cartridge assembly 300 from the operating site. Each group of fasteners 600 may correspond to the number of retention slots 308 or may correspond to only a part or portion of the number of retention slots 308 where for example multiple groups of fasteners 600 may be required to fully reload cartridge assembly 300.

Housing 200 may optionally receive elongate member 400 and fasteners 600 from an exterior source where, for example, multiple elongate members 400 may be attached or secured together during a procedure to provide additional fasteners 600 to cartridge assembly 300. For example, elongate body 30 may be adapted to provide elongate member 400 and fasteners 600 to housing 200 and may be adapted to allow a surgeon to feed additional elongate members 400 and fasteners into housing 200. In this way the number of fasteners 600 to be used may be tailored to a specific procedure or need of the surgeon.

Figure 13:
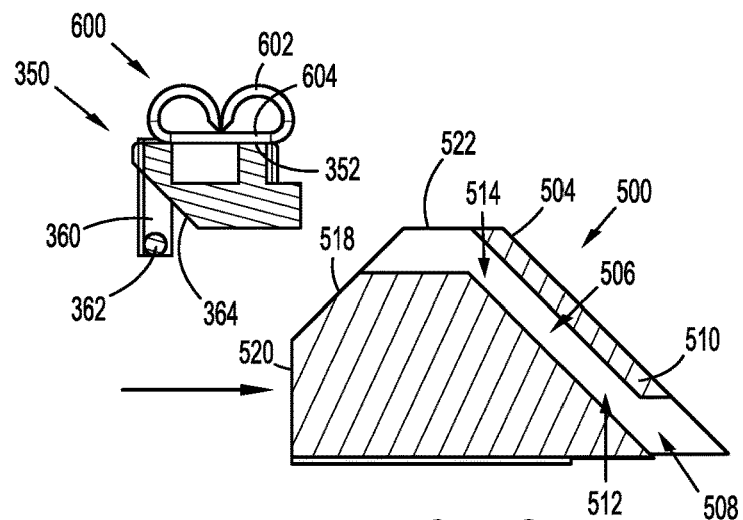
FIG. 13 is a view of FIG. 12 showing the pusher after the drive member has continued proximally.
Figure 14:
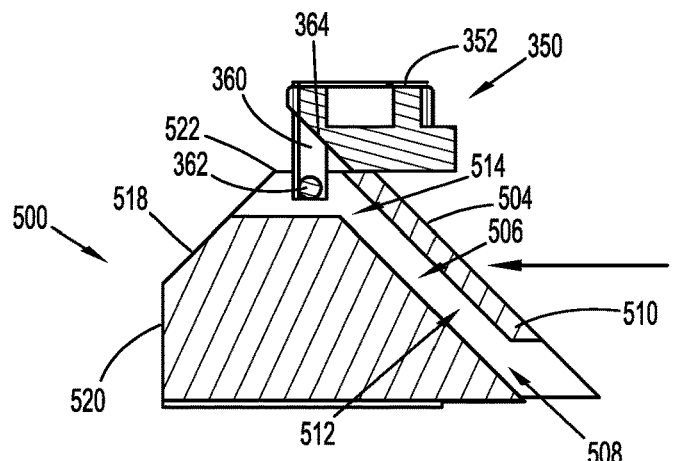
FIG. 14 is a view of FIG. 13 showing the drive member returning distally.
Figure 15:
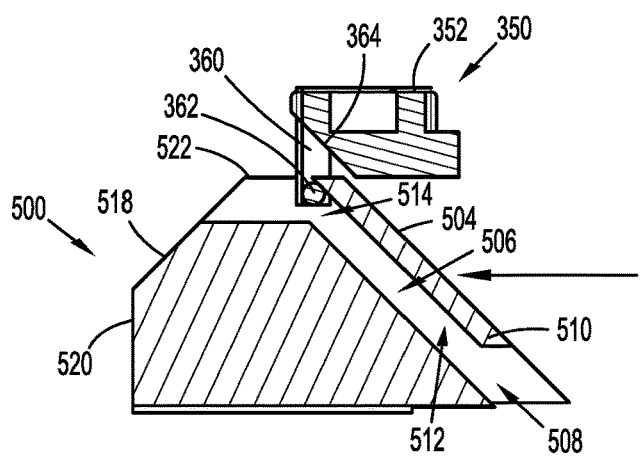
FIG. 15 is a view of FIG. 14 showing the outlet of the channel engaging the post of the pusher.
Figure 16:
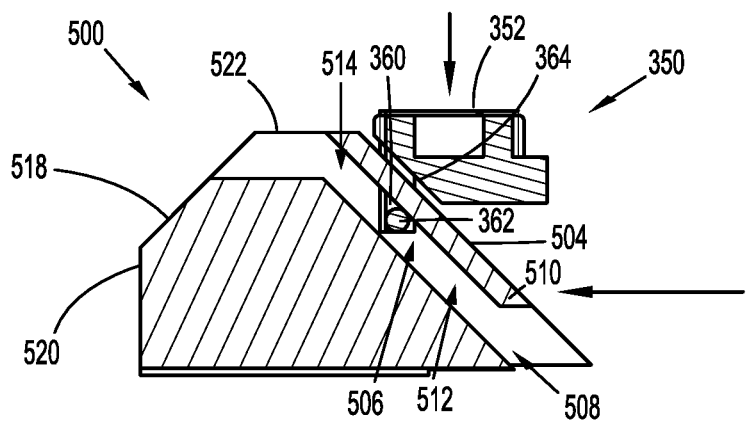
FIG. 16 is a view of FIG. 15 showing the post of the pusher engaging the channel to draw the pusher down the ramp of the drive member.
Figure 17:
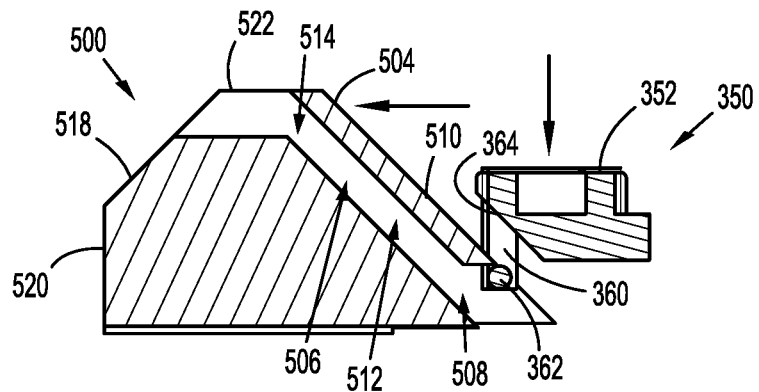
FIG. 17 is a view of FIG. 16 showing the pusher at the bottom of the ramp.
Figure 18:
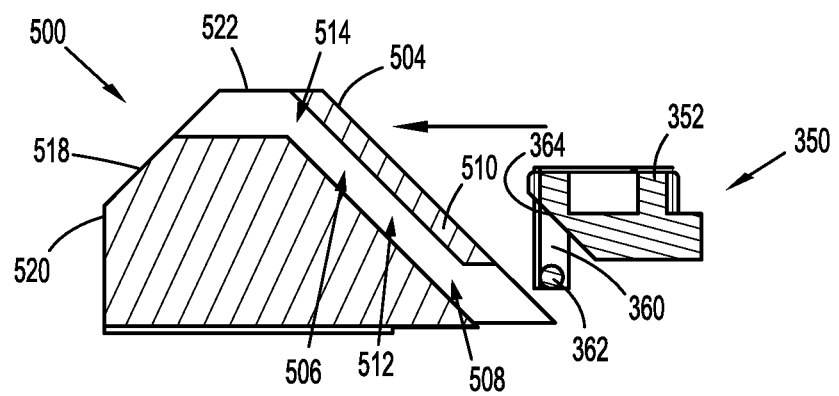
FIG. 18 is a view of FIG. 17 showing the pusher in pre-firing position with the drive member continuing to return distally.

During use, surgical stapling apparatus 10 is inserted into the surgical site and maneuvered such that tissue "T" is positioned between anvil assembly 110 and cartridge assembly 300. Handle assembly 20 is then actuated to close or approximate anvil assembly 110 and cartridge assembly 300 to grasp tissue "T" therebetween. After tissue "T" is grasped between anvil assembly 110 and cartridge assembly 300 actuator assembly 12 is actuated to translate drive member 500 proximally through cartridge assembly 300 from the initial position (FIG. 1A) to the fully fired position (FIG. 19) to fire a first group of fasteners 600. The surgical stapling apparatus 10 may come with the first group of fasteners 600 initially disposed within cartridge 300 and ready for firing or the first group of fasteners 600 may be translated into cartridge assembly 300 prior to firing. As discussed above, drive member 500 may optionally be translated only partially through cartridge assembly 300 to fire only a portion of the first group of fasteners 600 disposed within cartridge assembly 300. As drive member 500 translates through cartridge assembly 300, posts 362 of pushers 350 are engaged with inlet opening 508 and enter channel 512 (FIGS. 9 and 10). At the same time distal sloped surfaces 364 of pushers 350 engage ramps 504 of drive member 500 and translate or slide along ramps 504 to urge elongate member 400 and fasteners 600 toward retention slots 308 (FIGS. 11 and 12). As discussed above, fasteners 600 may engage guide surfaces 316 of retention slots 308 (FIGS. 4C-4E) to assist in guiding fasteners 600 through retention slots 308. Guide grooves 354 of pushers 350 engage backspans 604 and guide portions 606 of fasteners 600 to urge fasteners 600 through retention slots 308 (FIGS. 5G, 6A-6C, 12 and 19). As pushers 350 urge fasteners 600 through retention slots 308 fasteners 600 break through openings 404 of elongate member 400 where, for example, backspans 604 pass through slits 410 of openings 404. The elongate member may be adapted to allow the fasteners to break through the elongate member. Openings 404 may be torn or sheared to permit passage of fasteners 600 therethrough. A portion of each of pushers 350 may also pass through respective openings 404 of elongate member 400 during firing. Once fasteners 600 are urged through retention slots 308, legs 602 are deformed by the fastener deforming depressions 112 of anvil assembly 110 to thereby staple or fasten the tissue "T" clamped between anvil assembly 110 and cartridge assembly 300 (FIGS. 12, 13, and 19).

As drive member 500 translates proximally toward the fully fired position each fastener 600 is urged through a respective retention slot 308. After drive member 500 moves proximally past each of pushers 350 the fired pushers 350 remain in the fired position (FIGS. 13 and 19). Alternatively the fired pushers 350 may return at least partially toward the initial unfired position by sliding along ramps 518 on trailing portion 516 of drive member 500 after exiting distal portion 526 of channel 512.

Once firing is complete, actuator assembly 12 is actuated to translate drive member 500 back to its initial position. During translation of drive member 500 back to its initial position drive member 500 engages pushers 350 to return pushers 350 to the unfired position. For example, as seen in FIGS. 14-18, during distal movement of drive member 500, posts 362 of pushers 350 enter outlet opening 514 of channel 512 and engage channel 512 to draw pushers 350 down ramps 504. Posts 362 exit inlet opening 508 at the bottom of ramps 504 to return pushers 350 to the initial position. Pushers 350 are now ready to receive a new set of fasteners 600 from elongate member 400. Alternatively, pushers 350 may engage ramp 518 to slide towards peak portion 522 prior to posts 362 engaging channel 512 if pushers 350 did not remain in the fired position.

Elongate member 400 is then translated through housing 200 and cartridge assembly 300 by actuator assembly 12 to provide a second group of fasteners 600 to pushers 350 and retention slots 308. During this process, the empty openings 404 of elongate member 400 are translated distally past drive member 500 before returning to housing 200 via channels 306 or passageway 322 of cartridge assembly 300. For example, some or all of a second group of fasteners 600 may be translated into cartridge assembly 300 to partially or fully reload cartridge assembly 300. When elongate member 400 is positioned within cartridge assembly 300 such that a new set of fasteners 600 are aligned with retention slots 308 and the new set of fasteners 600 are supported on pushers 314, surgical stapling apparatus 10 is ready to be fired. It is contemplated that elongate member 400 may be translated through housing 200 and cartridge 300 to reload cartridge 300 before, during or after the translation of drive member 500 distally to the initial position.

The surgeon may then open or un-approximate anvil assembly 110 and cartridge assembly 300 to release the fastened tissue "T". Alternatively, the surgeon may reload cartridge assembly 300 during the release of tissue "T" or after releasing tissue "T". The surgeon may now maneuver surgical stapling apparatus 10 within the surgical site to position another portion of tissue "T" or another body tissue between anvil assembly 110 and cartridge assembly 300 as desired for further use of surgical stapling apparatus 10 without withdrawing surgical stapling apparatus 10 from the surgical site. For example, the surgeon may grasp a new portion of tissue between anvil assembly 110 and cartridge assembly 300, fire surgical stapling apparatus 10, and reload cartridge assembly 300 as describe above as many times as desired or necessary for the surgical procedure without removing surgical stapling apparatus 10 from the surgical site. This reduces the length of the surgical procedure, reducing the risk involved, and allows the surgeon to concentrate on the surgical procedure without dividing his attention between performing the procedure and reloading or replacing the surgical stapling apparatus 10 for further fastening of tissue.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. An end effector for a surgical stapling apparatus comprising:
   a cartridge defining a channel extending longitudinally therethrough and a plurality of slots extending through an upper surface thereof;
   an elongate member releasably retaining a plurality of surgical fasteners, the elongate member translatable through the cartridge;
   a plurality of pushers adapted to support the plurality of surgical fasteners, each pusher of the plurality of pushers having a post; and
   a drive member adapted to engage the plurality of pushers to urge the plurality of pushers towards the upper surface of the cartridge to urge the plurality of surgical fasteners through the plurality of slots, the post of each pusher engaging a lateral surface of the drive member.

2. The end effector according to claim 1, wherein the elongate member defines a plurality of openings configured to release the plurality of surgical fasteners through tearing of the plurality of openings.

3. The end effector according to claim 1, wherein the drive member includes an upper surface and an opposite, lower surface defining an inclined slot therebetween, the inclined slot configured to receive the post of at least one pusher of the plurality of pushers.

4. The end effector according to claim 1, wherein the plurality of surgical fasteners includes a first group of surgical fasteners and a second group of surgical fasteners.

5. The end effector according to claim 4, wherein the first group of surgical fasteners is urged through the plurality of slots when the drive member is moved to the fully fired position.

6. The end effector according to claim 4, wherein the elongate member is longitudinally movable to move the second group of surgical fasteners into alignment with the plurality of slots of the cartridge.

\* \* \* \* \*